(12) United States Patent
Pera

(10) Patent No.: US 6,679,255 B2
(45) Date of Patent: Jan. 20, 2004

(54) INHALING DEVICE FOR DISPENSING POWDERED MEDICAMENTS CONTAINED IN A CAPSULE THROUGH THE RESPIRATORY TRACT

(76) Inventor: Ivo E. Pera, 1400 St. Charles Pl., Pembroke Pines, FL (US) 33026

( * ) Notice: Subject to any disclaimer, the term of this patent is extended or adjusted under 35 U.S.C. 154(b) by 0 days.

(21) Appl. No.: 10/085,350
(22) Filed: Feb. 28, 2002

(65) Prior Publication Data
US 2002/0162552 A1 Nov. 7, 2002

(30) Foreign Application Priority Data
Mar. 1, 2001 (EP) .............................. 01104548

(51) Int. Cl.[7] .............................................. A61M 15/00
(52) U.S. Cl. ........................ 128/203.15; 128/203.12; 604/58; 604/59
(58) Field of Search .................. 128/203.12, 203.15, 128/203.17, 203.26, 203.37, 203.28; 604/58, 59, 60

(56) References Cited

U.S. PATENT DOCUMENTS

| | | | | |
|---|---|---|---|---|
| 3,918,451 A | * | 11/1975 | Steil | 128/203.21 |
| 3,921,637 A | * | 11/1975 | Bennie et al. | 128/203.15 |
| 3,973,566 A | * | 8/1976 | Mathes | 128/203.15 |
| 4,069,819 A | * | 1/1978 | Valentini et al. | 128/203.15 |
| 4,098,273 A | * | 7/1978 | Glenn | 128/203.15 |
| 4,105,027 A | * | 8/1978 | Lundquist | 128/203.15 |
| 4,117,844 A | * | 10/1978 | James | 128/203.15 |
| 4,206,758 A | * | 6/1980 | Hallworth et al. | 128/203.15 |
| 4,210,140 A | * | 7/1980 | James et al. | 604/58 |
| 4,353,365 A | * | 10/1982 | Hallworth et al. | 128/203.15 |
| 4,846,168 A | * | 7/1989 | Abiko et al. | 128/203.15 |
| 5,263,475 A | * | 11/1993 | Altermatt et al. | 128/203.15 |
| 5,337,739 A | * | 8/1994 | Lehman | 128/205.27 |
| 5,337,740 A | * | 8/1994 | Armstrong et al. | 128/203.12 |
| 5,349,947 A | * | 9/1994 | Newhouse et al. | 128/203.21 |
| 5,372,128 A | * | 12/1994 | Haber et al. | 128/203.21 |
| 5,522,383 A | * | 6/1996 | Calvert et al. | 128/203.15 |
| 5,651,359 A | * | 7/1997 | Bougamont et al. | 128/203.15 |
| 5,669,378 A | * | 9/1997 | Pera et al. | 128/203.21 |
| 5,787,881 A | * | 8/1998 | Chawla | 128/203.15 |
| 5,797,391 A | * | 8/1998 | Cook et al. | 128/203.15 |
| 6,012,454 A | | 1/2000 | Hodson et al. | |
| 6,092,522 A | * | 7/2000 | Calvert et al. | 128/203.21 |
| 6,230,707 B1 | * | 5/2001 | Horlin | 128/203.15 |
| 6,470,884 B2 | * | 10/2002 | Horlin | 128/203.15 |

FOREIGN PATENT DOCUMENTS

| | | |
|---|---|---|
| EP | 0388621 | 9/1990 |
| GB | 2064336 | 6/1979 |
| GB | 2253200 | 1/1991 |

* cited by examiner

Primary Examiner—Weilun Lo
Assistant Examiner—Michael Mendoza
(74) Attorney, Agent, or Firm—Malin, Haley & DiMaggio, P.A.

(57) ABSTRACT

An inhaler capable of administering powdered medicaments contained in a capsule is formed by a compartment housing the capsule, inside the cover or the body of the inhaler, and a cutting element, inside the same cover or the body. The element cuts or perforates the capsule, releasing the substance it contained. The powder falls into a grid reservoir below that holds the pieces of the case end lets only the powder pass through. Once the capsule is inserted into the compartment, it will be sufficient to activate the cutting device, then place the mouthpiece into the mouth and breathe in, so that the powdered substance dispersed into the chamber can reach the lungs. The inhaler may be equipped with disposable accessories to be placed into the mouth, otherwise it may be used with specific accessories for inhaling the substances also by the nose.

37 Claims, 7 Drawing Sheets

FIG. 1
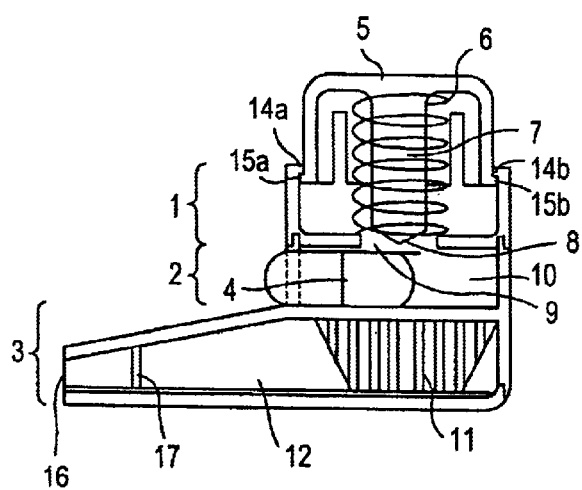
FIG. 2
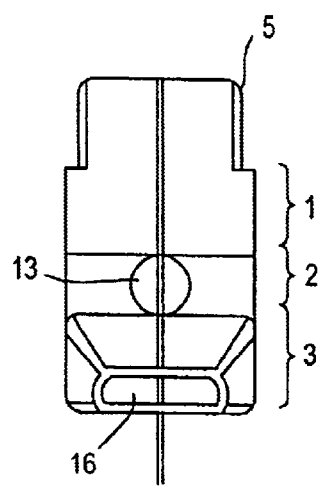
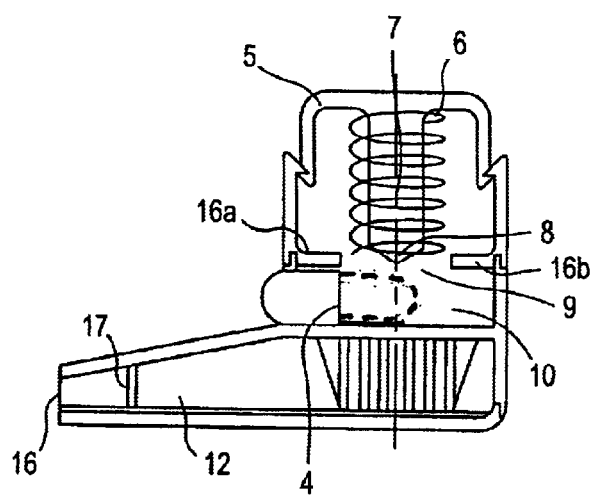
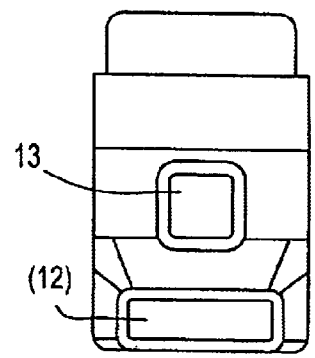

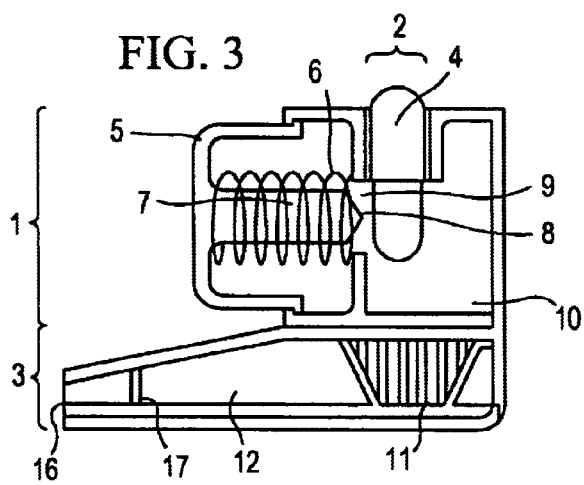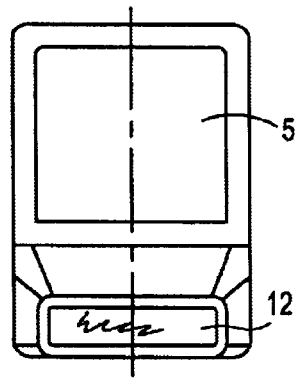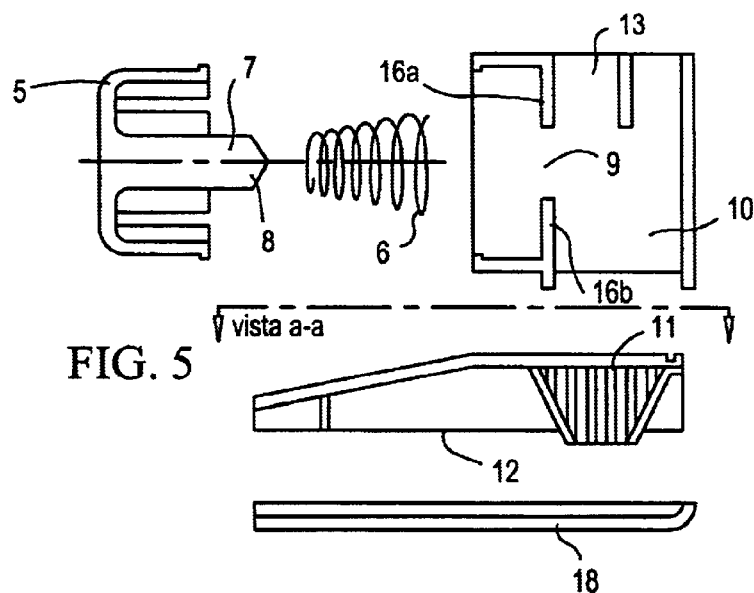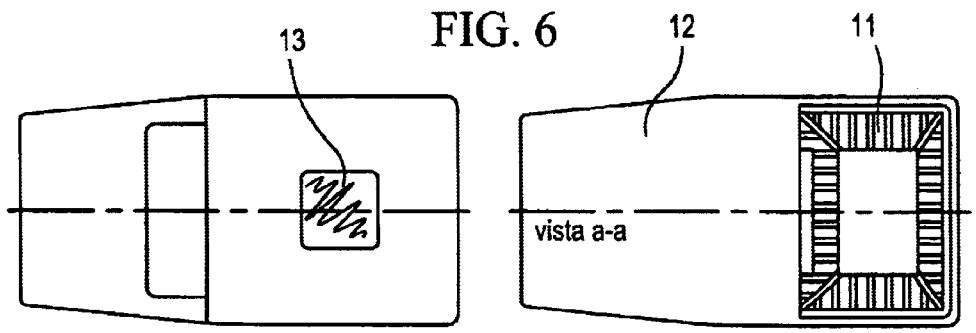

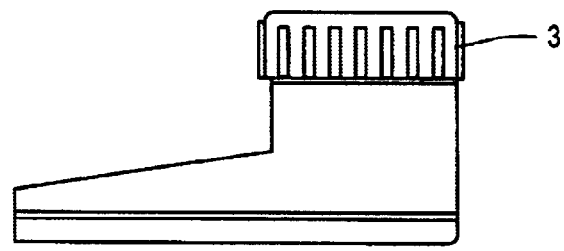
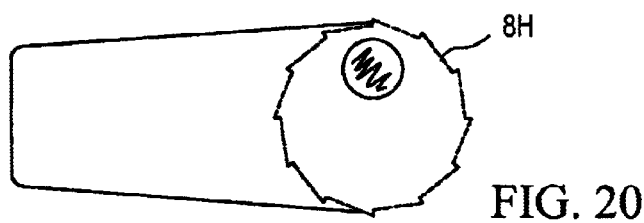
FIG. 20
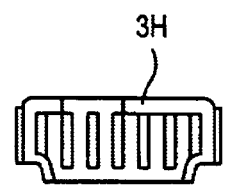
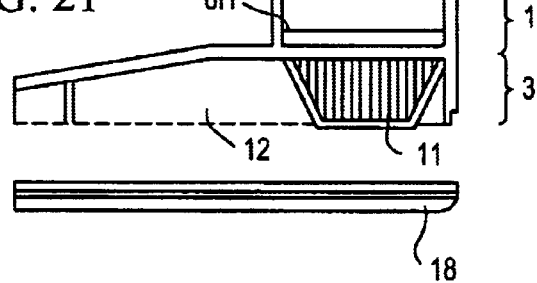
FIG. 21
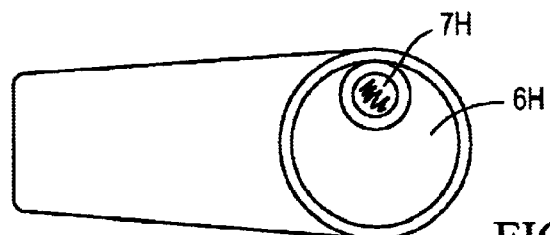
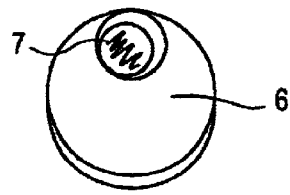
FIG. 22

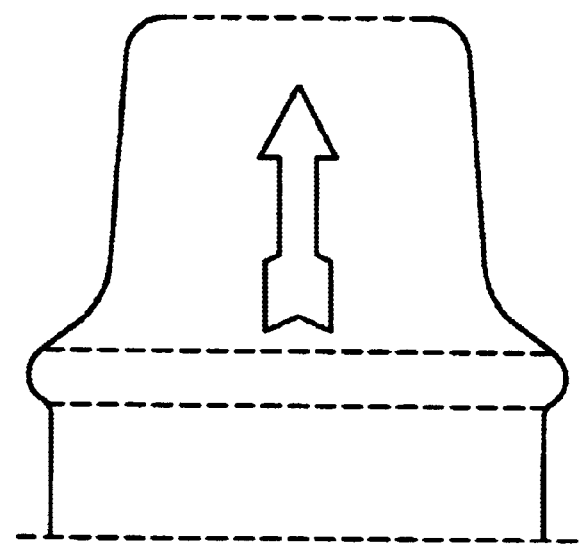
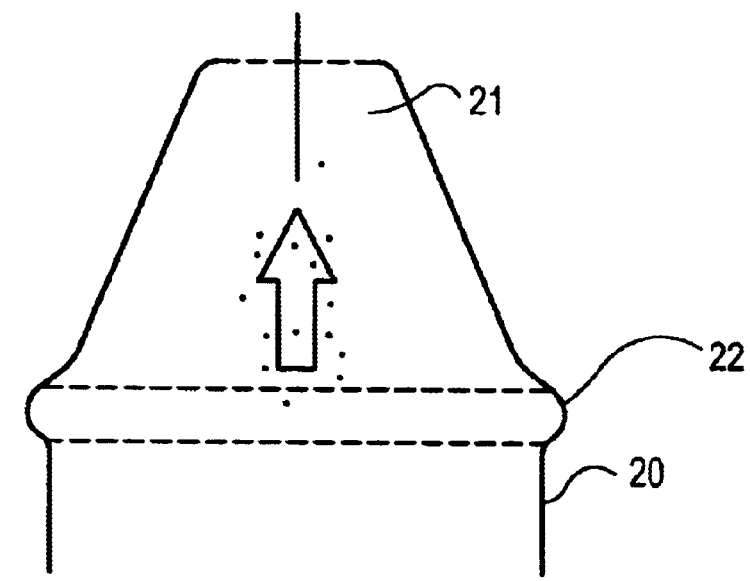
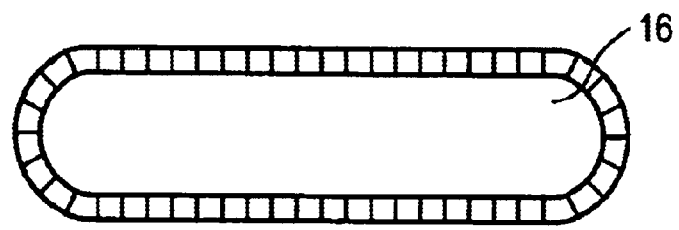
FIG. 23

INHALING DEVICE FOR DISPENSING POWDERED MEDICAMENTS CONTAINED IN A CAPSULE THROUGH THE RESPIRATORY TRACT

DESCRIPTION

This application claims the benefit of and priority to European Application No. EP01104548.1, filed Mar. 1, 2001.

TECHNICAL FIELD

The present invention relates to an Inhaling Device capable of administering only one dose of powdered medicaments at a time, to use in Respiratory Therapy and other Diseases through the topical administration of Medications through the mucous linings of tracheo-bronchial tree and the lungs.

BACKGROUND ART

As the lung is considered to be one of the more effective, noninvasive route of administration to the systemic circulation, a number of powdered medications can be used to treat a variety of conditions that accompany a lot of different diseases. Conditions requiring an inhaler, particularly in such therapy where can be administered to a patient on a program of home care, include: (1) infection, (2) mucous edema, (3) tenacious secretions, (4) foam buildup, (5) bronchosplasms, and (6) loss of compliance.

Many useful medicaments, and especially penicillin and related antibiotics, are subject to substantial or, in some instances, complete alteration by the stomach juices when administered orally. Different patients will react differently to the same dosage at different times. On this account, in past oral dosages was supplemented by checking blood samples to ascertain how much medicament has found its way into the blood stream, or by parental administration.

Powdered medicaments administered by inhalation are not frequently used for delivery into the systemic circulation, because of various factors that contribute to erratic or difficult-to-achieve blood levels. Whether or not the powder drugs reaches and is retained in pulmonary alveoli depends critically upon particle size. The literature reports that the optimum particle size for penetration into the pulmonary cavity is of the order of ½ to 7 um.

The general properties given rise to errors of such inhalers in dispensing proper Medicaments are specific directional and velocity characteristics including instability and concentration of the mass of particles administered in a unit volume of air. Moreover in a definitive clinical setting the patient's inhaling flow can vary significantly. During my research and development I have considered appropriate to test several types of Inhalers with different flow rate in order to develop a novel Inhaling Device, which is obviating the above described disadvantage, by effectively and smoothly inhaling one dose of powdered medicaments at a time into the pulmonary tract by the simple inspiration of air by a patient.

Several devices have been developed for the administration of micronized powders of relatively potent drugs, even if, at present, devices capable of dispersing dry powders contained in a capsule are not known at all. The Norisodrine Sulfate Aerohaler Cartridge (Abbott) is an example of such product. In the use of this Aereohaler, inhalation by the patient causes a small ball to strike a cartridge containing the drug. The force of the ball shakes the proper amount of the powder free, permitting its inhalation. Another device, the Spinhaler (Fisons), TurboHaler from Astra are propeller-driven device designed to deposit a mixture of lactose and micronized cromolyn sodium into the lung, other devices developed by Glaxo, such as Rotahaler, Beclodisk, Diskhaler, Ventodisk and Diskus, all for the administration of powdered drugs for the Respiratory Tract (like Ventolin, Albuterol, Salbritanol, Serevent, etc.) and several other types of these inhalators at present on the market, however most are cumbersome, complicated and expensive. Consequently, these multi-dose devices have to be reused, whereas for reasons of hygiene and, particularly owing to the difficulty of keeping the mouthpiece clean, it would be proper and more convenient to have available an inhalator which can be disposed after one single use. Additionally present devices often result in problems of obtaining a proper mixture with the air during the transmission of the medication to the breathing portions of the body thereby affecting efficiency of the medicinal mixture.

But even if it's preferable to use this devices just once, the invention that is object of this patent has been realized in two embodiments: the first one is a disposable inhaler, while the second one can be used more times.

Clinical practice patients, who are often elderly people, find it difficult to understand the multi-disk method of loading and administering the dry powdered medicament. The illustrative page enclosed with the medicine, though clear, is nevertheless only theoretical. In synthesis everything is seen as complex and difficult and is thus refused. There is the actual possibility that the medicine is not administered because the patient has not noticed that the loader is empty after several doses. Then there are hygienic needs to clean the mechanism with the special brush, etc.

All this frequently results in the premature abandoning of the medicinal formulation, possibly to return to the spray. This, despite its apparent simplicity of use and rapidity, is liable to constant errors, both on the part of the patient and on the part of the nurses, so the spray is almost always delivered on the tongue and not in the lower respiratory tract, leading to repeated doses, with possible cumulative side effects. The serious matter is that the dry powder preparations are almost unknown even in the hospital environment, where the priority in potency and dignity of the "pill" medicine still exists, as it does outside the hospital.

DISCLOSURE OF INVENTION

The elimination of these obstacles which compromise the use of a decisive weapon such as the one object of this invention, is thus desirable. The development of the Inhaling Device proposed is needful, to properly dispense powered medicines, and for other similarly interesting applications with potentially enormous developments which can be hypothesized for other substances such as:

Agents useful for calcium regulation (e.g., calcitonin, parathyroid hormone, and the like):

Analgesic/antipyretics (e.g., aspirin, acetaminophen, ibuprofen, naproxen sodium, buprenorphine hydrochloride, propoxyphene hydrochloride, propoxyphene napsylate meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalburphine hydrochloride, mefenamic acid, butorphanol tartate, choline salicylate, butalbital, phenyltoloxamine citrate, diphenhydramine citrate, methotrimeprazine, cinnamedrine hydrochloride, meprobamate, and the like);

Antianginal agents (e.g., beta-adrenergic blockers, calcium channel blockers (e.g., nifedipine, diltiazem hydrochloride, and the like), nitrate (e.g., nitroglycerin, isosorbide dinitrate, pentaerythritol tetranitrate, erythrityl tetranitrate, and the like);

Antidepressant (e.g., doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

Antianxiety agents (e.g., lorazepam, buspirone hydrochloride, prazepam, chlordiazepoxide hydrochloride, oxazepam, chlorazepate dipotassium, diazepam, hydroxyzine pamoate, hydroxyzine hydrochloride, alprazolam, droperidol, halazepam, chlormezanone, and the like);

Antiharrythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

Antiarthritic agents (e.g., phenylbutazone, sulindac, penicillamine, salsalate, piroxicam, azathioprine indomethacin, meclofenamate sodium, gold sodium thiomalate, ketoprofen, auranofin, aurothioglucose, tolmetin sodium and the like);

Antibacterial agents (e.g., amikacin sulfate, aztreonam, chloroamphenicol, chloramphenicol palmitate, chloamphenicol sodium succinate, cirpofloxacin hydrochloride, clindamycin hydrochloride, clindamycin palmitate, clindamycin phosphate, metronidazole, metronidazole hydrochloride, gentamicin sulfate, licomycin hydrochloride, tobramycin sulfate, vancomycin hydrochloride, polymyxin B sulfate, colistimethate sodium, colistin sulfate and the like);

Anticoagulants (e.g., heparin, heparin sodium, warfarin sodium, and the like);

Anticonvulsants (e.g., valproic acid, divalproate sodium, phenytoin, phenytoin sodium, clonazepan, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

Antidepressant (e.g. doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, no:rtriptyline, amitriptyline hydrochloride, isosarboxazid, desipramine hydrochloride, trimipramine maleate, protriptyline hydrochloride, and the like);

Antifibrinolytic agents (e.g., aminocaproic acid);

Antifungal agents (e.g., griseofulcin, keloconazole, and the like);

Antigout agents (i.e., colchicine, a'iopurinol and the like);

Antihypertensive agents (e.g., trimethaphan camsylate, phenoxybenzamine hydrochloride, pargyline hydrochloride, desertpidine, diazoxide, guanethidine monosulfate, minoxidil, rescinnamine, sodium nitroprusside, rauwolfia serpentina, alseroxylon, phentolamine mesylate, reserpine, and the like);

Anti-infectives (e.g., GM-CSF);

Antimanic agents (i.e., lithium carbonate);

Antimicrobials (e.g., cephalosporins (e.g., cefazolin sodium, cephradine, cefaclor, cephapirin sodium, ceftisoxime sodium, cefoperazone sodium, cefotetan disodium, cefutoxime azotil, cefotaxime sodium, cefadroxxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, ceforanide, ceftraxone sodium, ceftazidime, cefadroxil, cephradine, cefuroxime sodium and the like), penicillins (e.g., ampicillin, amoxicillin, penicilling benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, pinicillin G potassium, penicillin G procaince, methicillin sodium, nafcillin sodium, and the like), erythromycins (e.g. erythromycin ethylsuccinate, erythromycin, erythromicin estolate, erythromycin lactobionate, erythromicin siearate, erythromicin ethylsuccinate, and the like) tetracycline (e.g., tetracycline hydrochloride, doxycycline hyclate, minocycline hydrochloride, and the like), and the like);

Antimigraine agents (e.g., erotamine tartrate, propanolol hydrochloride, isometheptene mucate, dichloralphenazone, and the like);

Antinauseant/antiemetics (e.g., meclizine hydrochloride, nabilone, prochlor-perazine, dimenhydrinate, promethazine hydrochloride, thiethylperazine, scopolamine, and the like);

Anti-oxidants (e.g., beta-carotene, butylated hydroxynisole, butylated hydroxy-toluene, catalases, coenzyme Q10, glutathione, copper sebacate, folic acid, manganese, retinol, pycnogenol, selenium, superoxide dismutase, lycopene, lipoic acid, acetyl-l-carnitine, N-acetyl cysteine, linoleic acid, vitamins A, B2, B6, B12, C and E, taurine, zinc, adenosine, allicin, aloe, alpha lipoic acid, BHA, BHT, bilirubin, capsaicin, catechin, cysteine, coumarin, curcumin, dimethylglycine, glycine, ferrous fumarate, genistein, ginger, ginkgo biloba, gallates, gluconate, green tea, isoascorbic acid, L-glutamine, L-methyl methionine, L-seleno cysteine, L-seleno methionine, lutein, melatonin, methionine reductase w(Cu—Zn or Mn), N-acyl l-cysteine esters, N-acyl l-methionine esters, poplar bud, procyanidin, pycnogenol, resveratrol, rosmary, rutin, rutinose, selenium-yeast, seleno cysteine, seleno methionine, silybum marianum, sodium bisulfite, sodium metasulfite, sodium sulfite, sodium thiosulfite, spirulina, sulfuraphane, superoxide dismutase (SOD), taurine, thioglycerol, thiol, thiosorbitol, thiourea, wheat grass, zinc gluconate and the like);

Antiparkinson agents (e.g., ethosuximide, and the like);

Antiplatelet agents (e.g., aspirin, empirin, ascriptin, and the like);

Antistamine/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate, and the like);

Antipsychotic agents (e.g., haloperidol, loxapine succinate, loxapine hydroxhloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

Antiulcer/antireflux agents (e.g., famotidine, cimetidine, ratitidine hydrochloride, and the like);

Antiviral agents (e.g., interferon gamma, zidovudine, amantadine hydrochloride, ribavirin, acyclovir, and the like);

Bronchiodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g. aminophylline, dyphylline, metaproterenol sulfate, aminophylline), mast cell stabilizers (e.g., cromolyn sodium), inhalant cortisteroids (e.g., flurisolidebeclomethasone dipropionate, beclomethasone dipropionate monohydrate), salbutamol, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

Hemorheologic agents (e.g., pentoxifylline);

Hypoglycemic agents (e.g., human insulin, purified beef insulin, purified pork insulin, glyburide, chlorpropamide, glipizide, totalbutamide, tolazamide, and the like);

Hypolipidemic agents (e.g. clofibrate, dextrothyroxine sodium, probucol, lovastatin, niacin, and the like);

Hormones (e.g., androgens (e.g., danazol, testosterone cypionate, fluoxymesterone, ethyltostosterone, testosterone enanihate, methyltesterone, fluoxymesterone, testosterone cypionate), estrogens (e.g., estradiol, estropipate, conjugated estrogens), progestins (e.g.methoxyprogesterone acetate, norethindrone acetate), cortisteroids (e.g. triamcinolone, betamethasone, betamethasone sodium phosphate, dexamethasone, dexamethasone sodium phosphate, dexamethasone acetate, prednisone, methylprednosolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like;

Nucleic acids (e.g., sense or anti-nucleic acids encoding any protein suitable for delivery by inhalation, including the proteins described herein, and the like);

Proteins (e.g., DNase, alginase, superoxide dismutase, lipase, and the like);

Sedatives/hypnotic (e.g., ergotamine tartrate, propanol hydrochloride, isomeheptene mucate, dichloralphenazone, and the like);

Thrombolytic agents (e.g., urokinase, streptokinase, altoplase, and the like).

Additional agents contemplated for delivery employing the invention inhalation device and methods described herein include agents useful for the treatment of diabetes (e.g., activin, glucamon, insulin, somatostatin, proinsulin, amylin, and the like), carcinomas (e.g., taxol, interleukin-1, interleukin-2, (especially useful for treatment of renal carcinoma), and the like, as well as leuprolide acetate, LHRH analogs (such as nafarelin acetate), and the like, which are especially useful for the treatment of prostatic carcinoma), endometriosis (e.g., LHRH analogs), uterine contraction (e.g., oxytocin), diuresis (e.g., vasopressin), cystic fibrosis (e.g., Dnase (i.e., deoxyribonuclease), SLPI, and the like), neutropenia (e.g., GCSF), lung cancer (e.g., beta 1-interferon), respiratory disorders (e.g. superoxide dismutase), RDS (e.g., surfactants, optionally including apoproteins), and the like.

Presently preferred indications which can be treated employing the invention inhalation device and methods described herein include diabetes, carcinomas (e.g., prostatic carcinomas), bone disease (via calcium regulation), cystic fibrosis and breathing disorders (employing bronchodilators), and the like. Accordingly, there exists a definite need for a tiny disposable dry powder pharmaceutical delivery device that can use many different powdered pharmaceuticals, which can safely stored to maintain stability until dispensing, without any loss of uptake efficiency due to its advanced design, or to excessive absorption within the mouth or throat. There is a further need for such a device to be conveniently disposable without being overly expensive. The present invention satisfies these needs and provides further related advantages.

A further advantage of the device of the present invention may be represented by an additional protective factor constituted by reduction of oral mycosis, notoriously correlated with the fact that the spray is nearly always deposited in the area of the tongue and oropharynx, also as a result of the backwards direction of the spray itself. This is eliminated with the optimal micronization obtained with the disposable method.

The clinical, pharmacological, economic and finally the social advantages can be anticipated together with the co-operation of the patient (it is sufficient to consider the reduction of anxiety due to the easiness to use the device, the fact that the patient no longer needs the assistance of members of the family, with the reduction of injections, and with lower hospitalization required, etc.)

From studies made by the inventors and from specialist practitioners, as well as from the exchanging of experiences with general practitioners who are called to put into practice the prescriptions of the pneumologist, the therapy with such deficient multi-dose inhalators tends to limit itself, whereas it would be desirable to consider it as a separate and autonomous entity as compared to the aerosol which is often confused with the ready-to-use type. In fact from this point of view it is overtaken by old systemic medicines (theophylline) which thanks to their necessary regular use space from the B2-stimulants, because they manage to impose a constant and observed rule which is easy to understand.

Therefore the desire of the specialist, but also and especially of the general practitioners to have these potent and precise arms available springs from the above, but with less complexity of use, in order to widen the base of subjects who are the potential users and beneficiaries.

Theoretically possibilities spring from analytical reflection and although they come from someone who does not by profession program company strategies and methods, they offer nevertheless serious and concerned criticism.

In my opinion these solutions are represented by the total upending of the concept of administration, where first of all the interest compliance and serenity of the patient is favoured (many speak of anxiety in complex manoeuvres) where he is called to execute the minimum number of actions possible and with a strong temporal and material connotation, i.e. with a precise identification of the act performed in the same way as the taking of any pill, with the result of the exact perception of the completed event (let us not forget that the patient often doubts that he has correctly administered the medicine via aerosol). Consequently there is a strong concentration of faith in the act itself, which as well as scientific becomes "magical", therefore saving and above all worthy of faithfulness.

The regular imposition of the right doses is not the least of the advantages of the methodologies in question. The possibility of lower production costs and the better perception of results by the prescribing doctor, and hence the increase of confidence in the medicinal formulation, is another advantage of the methodology which cannot be ignored.

The use of the breath-activated inhaler of the present invention is extremely simple, foolproof, and the user will easily achieve maximum control of his health, instead the more complicated models available on the market, anyone using them will be given extensive training for its use. Nevertheless it is generally estimated that with the standard inhaler only about ten percent (10%) of the inhaler drug actually reaches the lungs, the remaining ninety percent (90%) is deposited on the lining of the mouth and throat, and when relief is not forthcoming, the inhaler use tends to quick press for another dose of the drug. Using such inhalers to often is likely, under certain circumstances to have serious unpleasant side effects, such as mild irritation in the throat, dysphonia, nausea, jitteriness, indigestion, gastric reflux, insomnia, thrush, hoarseness, coughing, oropharyngeal candidasis, etc.

The use of the Inhaler proposed by the present invention through the respiratory tract may provide an efficient means of administering dry powder medicaments such as vasoconstrictors, antihistaminics, antispamodics, antipeptics, antibronchiolitis, B2-stimulants-corticosteroids, antivirals, antifungals, antioxidants, antileukotrienes, antiallergens, antibiotics, human proteins, peptides, etc., which will generally requires a smaller dosage than would be necessary if the drug were given systematically, infection is often accompanied by one or more of the five other conditions cited above.

The principal purpose of the present invention is to provide an Inhaling Device for dispensing only one dose of powdered medicaments at a time into the Respiratory Tract and is intended to be easy to use, inexpensive and then be thrown away when it has served its purpose, even if, in a second embodiment of this invention, it can be used more times.

The present invention relates to an Inhaling Device suitable for delivery, via the respiratory tract, therapeutic medication and includes among its objects and advantages increased convenience in medication with dry medicaments in powder form, especially with respect to accuracy of dosage and accurate placement of the drug.

The inhaler object of this invention is useful also with antibiotics, steroids and other difficulty soluble compounds. Problems associated with the formulation of this drug include aggregation, caking, particle-size growth and often clogging, which using the present Inhaler is completely avoided.

It has been discovered that the use of the Inhaler of the present invention for dispensing powdered medicaments available in the form of fine powders, can be practiced to cause effective therapeutic effect. It is also possible to combine the general treatment thus resulting with high local concentration of the same medicament in the respiratory tract.

Solid inhalation therapy is of value in connection with many therapeutic agents, including antiseptic bronchiolytics, and vaso-constrictors, and is indicated for at least some of the known anti-histamine drugs.

Many therapeutic agents which are water soluble, will be found effective by solid inhalation, by both the effect and the degree of effectiveness need to be established by specific test in connection with each substance.

Many ingredients can be added as Membrane Permeation Inhaler to the Drug formulations to increase their barrier permeability, but the preferred one and most effective is lactose.

Accordingly, the present invention will succeed in obtaining such constancy by providing a device which is to be utilized by the patient by breathing in, in a simple, substantially normal way. Utilized the energy of the air flowing through the device to deliver into the lining a single dose of powdered medicaments at a time, which charge is delivered quickly, shortly after inhalation begins, and finds its way to its resting place. Thus the device itself and the body passages first receiving the stream of air are thoroughly swept and scavenged with pure air during a major portion of the breathing-in process. I have found that administration in this way not only contributes to deep penetration of the medicament, but that it becomes unnecessary to pulverize or micronize the medicament into a true smoke. The use of larger particle tends to increase the reliability with which a uniform fraction of the material will pass on through the body passages first receiving the stream without getting caught on the moist walls.

With the Inhaler proposed by the present invention the absorption is virtually as rapid as the drug can be delivered into the alveoli of the lungs, since the alveolar and vascular epithelial membranes are quite permeable, blood flow is abundant, and there is a very large surface for absorption.

It is an object of this invention to provide an extremely simple device which is sturdy, dependable, reliable, foolproof and which will maintain its characteristics for a long period so that if a considerable time about elapse between the original manufacture of the item and its utilization, the therapeutic efficacy of the drug will remain comparatively undiminished.

This invention makes possible to dispense any type of powdered drugs which are at all times completely under the control of the user. It will thus be seen that the invention provides a simple and convenient means of dispensing powdered drugs, and it is capable of extremely wide applications.

The Inhaling Device of this invention can be manufactured quite easily using means of injection mouldings well known in the art, thereby affecting substantial cost reduction in manufacturing the device without adversely affecting the medicament administration inhalation.

With this and other objects in view the invention consists in the details of an inexpensive but efficient inhalator, convenient and easy to use and of low cost to the user so that the device may be discarded following the single administration of the contained medicament.

As can you see from the drawings included, the concept in question is carried out through the use of disposable administration devices which can be adapted in their dimensions, external aspect and internal and external conformation: however, all the devices follow the logic of a single and exact dose of medicine in a container made of plastic, or other appropriate material which can also be biodegradable, and suitable for inhalation, thanks to its conformation.

An Inhaling Device for dispersing through the respiratory tract only one dose of powdered medicaments contained in a capsule at a time, according to the invention, comprises:

means to hold the capsule (4) with a compartment (13), located inside the cover or inside the chamber close to it, into which the capsule is inserted for about half its length and is held still during the operation of incision so as to guarantee the dispersion of the powder it contains;

means to split the capsule, with a cutting element equipped, on one end, with a blade and/or point;

means to release the powder contained in the capsule, with a body formed by one or more chambers (1) (2) that contain the capsule and the cutting device, connected to a chamber (3) set to hold the powder produced after the breakage of the capsule;

means to hold the pieces of the case of the capsule, after it has been split, and to prevent the powder from aggregating, with a reservoir (11) having a series of slots on its walls that hold the bigger pieces inside, while letting the powder enter the chamber (12);

means to deliver the powder of the capsule released into the lower chamber of the inhaler, with a mouthpiece (16) from which the user can inhale the powder;

optional means to filter the powdered drug, in the portion immediately before the final part of the opening of the inhaler, with a porous filter (17) capable of holding any possible piece of the drug not completely pulverized.

Conveniently, with reference to FIGS. 1, 2, 3, 4, 5 and 6, the capsule is cut by the point connected to the cover, which moves up and down by means of a spring. This system comprises:

means to hold and split a capsule (4) and then release the powder it contained, with a body consisting of a chamber (1), equipped with a cover (5) at one end, and a chamber (2) at the opposite end, which is connected to said chamber (1) and is closed at the bottom by a chamber (3) connected to said chamber (2);

means to hold the capsule inside said chamber (2), with an open compartment (13) into which the capsule (4) is placed, resting on the circular groove of said compartment (13), and filling the hollow portion (10) of the chamber (2);

means to hold the pieces of the case of the capsule (4), after it has been split, and to prevent the powder from aggregating, with a grid reservoir (11) having a series of slots on its walls that hold the bigger pieces inside, while letting the powder pass through;

means to close the container comprising the capsule, with a cover (5) which enters the chamber (1) and has two outer protrusions (14a, 14b) on its walls that stop under the inner protrusions (15a, 15b) of the chamber (1), preventing the cover from accidentally escaping from its place;

means to allow the cover (5) to move perpendicularly to the capsule (4) till the stop of said protrusions, with a spring (6) inside the chamber (1), which touches the outer edge of the hollow portion (10) on its lower side and the inner surface of the cover on its upper side;

means to split the capsule (4), with said cover (5) having inside a pointed element (7) that passes through the elastic spring (6); when the cover (5) is pressed, it will perforate the capsule (4) placed into the hollow portion (10), releasing its powder into the chamber (12) and holding the pieces of the case in the reservoir (11);

means to deliver the powder of the capsule (4) released into the chamber (12), with a mouthpiece (16) from which the user can inhale the powder.

Conveniently, with reference to FIG. 1, the capsule (4) is located inside the compartment (13) in the hollow portion (10) in a horizontal position, while the cover (5) is in a vertical position; in this way, the element (7) will perforate the capsule (4) with its point (8), when the cover (5) is pressed down, in a vertical and perpendicular direction towards the capsule.

Conveniently, with reference to FIG. 3, the capsule (4) is located inside the compartment (13) in the hollow portion (10) in a vertical position, while the cover (5) is in a horizontal position; in this way, the element (7) will perforate the capsule (4) with its point (8), when the cover (5) is pressed laterally, in a horizontal and perpendicular direction towards the capsule.

Conveniently, in the above-illustrated solutions, the incision of the capsule releases the powder into the chamber (12) below, after it has been filtered by the reservoir (11).

Conveniently, with reference to the above figures, the body of the inhaler is formed by three parts that can be assembled each other: the chambers (1) and (2), and the chamber (3), besides a cover (5) that enters the chamber (1). Such a conformation facilitates the manufacturing and assembling of this device, considerably reducing the costs of the mass production.

Conveniently, with reference to FIGS. 1 and 2 the operation of incision of the capsule and the consequent inhalation of the powdered drug by the user, can be easily performed using just one hand: in particular, it's sufficient to keep the inhaler with your right hand, place your thumb under the base of the inhaler supporting it, and press the cover with your forefinger, so as to perforate the capsule; then you place the device into your mouth and inhale the powdered drug.

Conveniently, with reference to FIGS. 7, 8, 9, 10 and 11, the capsule is cut by means of the rotation of the cover of the inhaler. This system comprises:

means to hold and split a capsule (4) and then release the powdered drug it contained, with a body consisting of a single chamber (1) in a horizontal position, equipped with an opening on the top, and closed at the bottom by a chamber (3) connected to it, so forming a single element;

means to hold the capsule inside the chamber (1), with an open compartment (13) into which the capsule (4) is placed in a horizontal position, resting on the circular groove of said compartment (13);

means to hold the pieces of the case of the capsule (4), after it has been split, and to prevent the powder from aggregating, with a reservoir (11), under the division point of the capsule, having a series of slots on its walls that hold the bigger pieces inside, while letting the powder pass through;

means to close the container (1) comprising the capsule, with a cover (2K) that closes the upper end of the chamber (1) and has two outer protrusions (14a, 14b) on its walls that stop under the inner protrusions (15a, 15b) of the horizontal chamber (1), preventing the cover (2K) from accidentally escaping from its place;

means to split the capsule (4), with a thin blade element (4K), connected to the cover (2K) and attached to its inner edge;

means to allow the cover (2K) to rotate, thanks to the circular shape of the same cover (2k) and the chamber (1), so as to split the capsule (4) with a simple rotation of the cover, in any direction, till the element (4K) reaches and cuts the capsule (4);

means to deliver the powder of the capsule (4) released into the chamber (3), with a mouthpiece (16) from which the user can inhale the powdered drug.

Conveniently, the blade element (4k) is connected and perpendicular to the cover (2K) and to the capsule (4), so that, as it rotates following the rotation of the cover, it will cut part of the case of the capsule, removing it and letting the powder and the pieces of the same case fall into the reservoir (11) below, which lets only the powder enter the chamber (12) in order to be inhaled.

Conveniently, with reference to the above figures, the body of the inhaler is formed by two parts that can be assembled each other: the chambers (1) and (3), connected each other, besides the cover (2K) that enters the horizontal chamber (1). Such a conformation facilitates the manufacturing and assembling of this device, considerably reducing the costs of production.

Conveniently, with reference to the above figures, the operation of incision of the capsule and the consequent inhalation of the powdered drug by the user, can be easily performed by keeping the inhaler with one of your hands, and rotating the cover (2K) with the other one, until the blade element (4K) connected to the cover (2K) touches the lower part of the capsule (4); then you place the device into your mouth and inhale the powdered drug.

Conveniently, with reference to the above figures, the capsule (4) is inserted by the side wall of the chamber (1) into the suitable compartment (13), in a horizontal position. In order to prevent the capsule (4) from moving from its place, the lower edge of the cover (2K) has two outer protrusions (14a, 14b) on its walls that stop under the inner protrusions (15a, 15b) of the horizontal chamber (1), preventing the cover (2K) from accidentally escaping from its place and, at the same time, ensuring a greater stability of the capsule (4) during the operation of its incision.

Conveniently, with reference to FIGS. 12, 13, 14, 14B, 15, 16 and 17, the capsule is split by means of a cutting element that moves inside the unique horizontal chamber. This system comprises:

means to hold a capsule and then release the powder it contained, with a body consisting of a single chamber (1) in a horizontal position, equipped with an opening on the top, and connected at the bottom to a chamber (3) locked to it;

means to hold the capsule inside the only horizontal chamber (1), with an upper open compartment (13) into which the capsule (4) is placed in a vertical position, resting on the circular groove of said compartment (13);

means to hold the pieces of the case of the capsule (4), after it has been split, and to prevent the powder from aggregating, with a grid reservoir (11) below;

means to split the capsule (4), with a cutting element (7G), located inside the horizontal chamber (1), which comprises a system of two circular holes (8G) holding the lower part of the capsule (4) and having a vertical axis that coincides with the one of the inhaler;

means to allow the cutting element (7G) to move, with a rotating hinge at the end of the same element (7G) connected to an inner corner of the chamber (1), so that by pressing with a finger on the end portion (12G) of the cutting element (7G), it splits the capsule (4) in a horizontal direction, causing the dispersion of the powdered drug that will be later inhaled by the user;

means to deliver the powder of the capsule (4) released into the chamber (12), with a mouthpiece (16) from which the user can inhale the powder.

Conveniently, by pressing the end portion (12G) of the cutting element (7G), the hole (8G), which has a cutting inner perimeter and comprises a part of the capsule (4), moves in a horizontal direction, so that it removes the lower part of the case, letting the powder fall into the reservoir (11) below, together with the pieces of the case.

Conveniently, with reference to the above-illustrated practical solution, the cover is fixed and the capsule is inserted in a vertical position into the compartment (13) inside the cover, through a notch (3G) on the upper part of the cover.

Conveniently, with reference to FIG. 16, the hole (8G) of the cutting element (7G) that must split the capsule (4) located into the specific compartment (13), is formed by two circular holes of different diameter, having corresponding vertical axis with each other and with the vertical axis of the inhaler. The diameter of the hole (8a) on the upper part of the element (7G) is suitably smaller than the diameter of the hole (8b) on the lower part of the element (7G). This ensure a greater stability of the capsule (4) during the operation of its incision by means of the rotation of the element (7G); all that involves a complete dispersion of the powdered drug, preventing the capsule from moving upwards and consequently losing powder from the upper notch (3G) of the chamber (1).

Conveniently, with reference to the above figures, the body of the inhaler is formed by two parts that can be assembled each other: the chambers (1) and (3), connected each other, besides a cover (4G) that perfectly enters, by its lower edge, the horizontal chamber (1). Such a conformation facilitates the manufacturing and assembling of this device, considerably reducing the costs of production.

Conveniently, with reference to the above figures, the operation of incision of the capsule (4) and the consequent inhalation of the powdered drug by the user, can be easily performed by keeping the inhaler with one of your hands, and making the cutting element (7G) move with the other one, so that you press with your thumb on the end portion (12G) causing the element (7G) rotate around the fixed point (9G) where a rotating hinge is located.

Conveniently, the rotation of the element (7G) allows the system of the holes (8G) to split the capsule (4) and release the powdered drug; then you place the device into your mouth and inhale the powdered drug.

Conveniently, with reference to the above figures, the cutting element (7G) is made of plastic or other suitable material ensuring the necessary stiffness, so that it's sufficient a moderate force to split the capsule by means of the rotation of the cutting element.

Conveniently, with reference to FIGS. 18, 19, 20, 21 and 22, the capsule is cut by means of the rotation of the cover of the inhaler. This system comprises:

means to hold a capsule (4) and then release the powder it contained, with a body consisting of a chamber (1) in a horizontal position, equipped with an opening on the top and closed at the bottom by a chamber (3) connected to it. The horizontal chamber is closed on the top by a cover (3H) that comprises a compartment (13) of circular shape, inside which the capsule (4) is directly placed in a vertical position,;

means to hold the capsule inside said cover (3H), with an open compartment (13), of circular shape, placed directly inside the cover (3H), into which the capsule (4) is placed, resting on the circular groove of said compartment (13);

means to hold the pieces of the case of the capsule (4), after it has been split, and to prevent the powder from aggregating, with a reservoir (11) having a series of slots on its walls that hold the bigger pieces inside, while letting the powder pass through;

means to close the container (1), with a cover (3H), which holds the capsule (4) and closes the horizontal chamber (1), having two outer protrusions (12a, 12b) on its walls that stop under the inner protrusions (13a, 13b) of the chamber (1), preventing the cover (3H) from accidentally escaping from its place;

means to allow the cover (3H) to rotate, thanks to the circular shape of the same cover (3H) and the chamber (1), so as to split the capsule (4) with a simple rotation of the cover, in any direction, till a blade element (8H) reaches and cuts the capsule (4);

means to split the capsule (4), with an element (6H), consisting of a circular plate comprising a hole (7H), whose vertical axis is laterally moved from the one of the inhaler, which holds the lower part of the capsule (4), so that, by rotating said element (6H), the blade (8H) below cuts the lower part of the capsule (4);

means to filter the powder and the pieces of the case, with a reservoir (11) under the division point;

means to deliver the powder of the capsule released into the chamber (12), with a mouthpiece (16) from which the user can inhale the powder.

Conveniently, the lower part of the capsule (4) is inserted both into the hole of the element (6H) and into the corresponding hole below (7H) of the blade element (8H), which has a cutting inner circumference, so that, as the element (6H) rotates, while the blade element (8H) below is fixed, it will remove the lower part of the capsule (4), letting the powder fall into the reservoir.

Conveniently, the rotation of the cover (3H) permits the incision of the capsule (4); in this case, the capsule (4) remains in the specific compartment (13) that holds its upper part still, while its lower part is cut by the hole (7H) where it is inserted, following the rotation of the same cover.

Conveniently, with reference to the above figures, the capsule is directly inserted by the upper edge of the cover (3H), in a vertical position, corresponding to the external edge of the same cover (3H). In order to prevent the capsule (4) from moving from its place, the lower edge of the cover (3H) has two outer protrusions (12a, 12b) on its walls that stop under the inner protrusions (13a, 13b) of the horizontal chamber (1), preventing the cover (3H) from accidentally escaping from its place and, at the same time, ensuring a greater stability of the capsule (4) during the operation of its incision.

Conveniently, with reference to the above figures, the body of the inhaler is formed by two parts that can be assembled each other: the chambers (1) and (2), connected each other, besides a cover (3H) that enters the horizontal chamber (1). Such a conformation facilitates the manufacturing and assembling of this device, considerably reducing the costs of production. Conveniently, with reference to the above figures, the operation of incision of the capsule and the consequent inhalation of the powdered drug by the user, can be easily performed by keeping the inhaler with one of your hands, and rotating the cover (3H) with the other one, until the element (6H) connected to the cover (3H) touches the lower part of the capsule (4); then you place the device into your mouth and inhale the powdered drug. An accessory can be conveniently provided (FIG. 23): it's made of rubber or other suitable material and must be placed over the mouthpiece (16) of the inhaler, where it is locked thanks to its protrusion (22). In this way, the user inhales the powder from its opening (21) and substitutes the covering after each use. This device has such a size that allows it to be conveniently and easily carried in a handbag or even in your pocket. In a practical example, it is about 39 mm long and 29 mm high.

Conveniently, such a device can simplify and reduce the operations that must be performed for the inhalation of the powdered drug by the user; in particular, the shape and the position of the various chambers of the invention allow the user to perform the operation of incision of the capsule and the consequent inhalation of the powdered drug with a single hand, using a single finger to cause the incision of the capsule, a different finger according to each different solution. With the rest of the hand, he/she places the device into his/her mouth and inhales the powdered drug.

Conveniently, the powder released into the device is inhaled by the user by placing the outer end of the chamber, opposite to the grid reservoir, into his/her mouth and breathing in, so that the powder coming out from the opening enters the mouth and reaches the lungs.

Conveniently, this device is made of plastic material and should be thrown away after each use, so as to guarantee the greatest comfort.

Conveniently, this invention may also be used more times; in this solution, in order to ensure the greatest hygiene, it's possible to provide it with an accessory connecting the inhaler to the user's mouth, which must be substituted after each use.

Conveniently, under the housing portion of the capsule, a reservoir is provided, with a series of slots on its walls and a grid shape, which allows the pieces of the case of the capsule to remain inside the reservoir. Said reservoir has the important function to prevent the powder from aggregating in a humid atmosphere, obstructing in this way its dispersion into the chamber and the consequent inhalation by the user.

Conveniently, the spring (6) is made of metal, plastic or other suitable material ensuring the right flexibility, so that it's sufficient a moderate pressure to make it move.

Conveniently, in order to prevent the capsule (4) from moving from its place, and ensure a greater stability of the spring (6), a pair of fingers (16a) and (16b) are placed above or on one side of the capsule, accordingly to its horizontal or vertical position, consisting of a circular bend resting on the outer edge of the hollow portion (10) and a central hole allowing the point (8) of the cutting element (7) to pass through.

Conveniently, with reference to the figures of Tables 3/7 and 5/7, the cutting element is made of plastic or other suitable material ensuring the necessary stiffness, so that it's sufficient a moderate force to split the capsule by means of the rotation of the cover.

Conveniently, with reference to the figures of Tables 3/7 and 5/7, the cover can be totally pulled out from the horizontal chamber (1), so permitting to substitute the old capsule with a new one, in the case this device might be used more times.

Furthermore to obviate the above described disadvantages of the Inhalers of the prior art, the inventor developed the present "Inhaling Device for dispersing through the respiratory tract one dose of powdered medicaments contained in a capsule", providing the following advantages:

Easy to use, relieving the patient of mental tension and anxiety regarding the mode of administration and the immediate check of the completed operation.

Placebo effect advantage for the patient deriving from the psychological tranquillisation due to the simplicity of the method of administration, this being particularly relevant on old age patients.

Guarantee of the correct dosage and achievement of the therapeutic result, not only to benefit illiterate and elderly patients, but children too.

Optimum of the dispensing method due to its simplicity, dependability, reliability, fool-proof, and manufacturing low cost.

Will be discarded following the administration of the contained drug, avoiding the hygiene problems of the Multidose Devices which after the first time of its use can be bacteria contaminated and are easily soiled and subject to blockage.

Elimination of various Doctors reservations, which currently are not very much in favour to preserve extensively the use of powdered drugs through the use of inhalers.

Avoiding patient education and extensive training in how to use them, particularly for chronic therapies (many patients have difficulty with inhalers that require more than one step).

Efficacious and ready to be used with most powdered medicines, just to mention few but not limited to: antibiotics, mucolitics, antioxidants, hormone, vaccines, corticosteroids, etc., which are still not prescribed via inhalations due to lack of efficient devices and cultural instruction.

Elimination of the confusion between long-acting and ready-to-use medicines.

Resolution of the problem of patient co-operation.

Eye appealing and very small.

Moreover, the Inhaling Device in question eliminates manual problems, problems of maintenance, hygiene, comprehension, mistaken use and psychological conditions, and there is no doubt that the Inhaling Device of the present invention is the most uncomplicated and efficient method available for delivery powdered medicaments via the respiratory tract.

On the basis of what is stated, considering that the Inhaling Device is specifically dedicated to clinical use in the administration of powdered medicines which carry out their action locally on the respiratory tract or through the lung as noninvasive route of administration to the systemic circulation, it is held that this mechanism is capable of eliminating difficulties and uncertainty due to current methods of administration.

Inhaling Device Performance Data Test

According to the present state of the art for testing the efficiency of inhalers, I carried out representative tests comparing the Device of the present invention with several inhalers of the prior art.

My research for the experimental test has included basic scientific foundation of inhalation and applied aerosol science, comparative respiratory tract anatomy and physiology, inhalation exposure technique, selection of endpoints including applicable regulations and guidelines previously published by scientific literature to find a simple inhalation testing procedure to fulfil the assigned tasks to evaluate the efficiency of the Inhaling Device and to provide a foundation of my invention. The result ascertained by experiments of the rate of powdered drug scattered for the inhalers are shown in Table 1.

TABLE 1

COMPARISONS OF SCATTERING PROPERTY BETWEEN DRY POWDER INHALERS

| Dry Powder Rate of Scattered Inhalers | Rate of Dry Powder | Rate of Dry Powder |
|---|---|---|
| Dry Powder (D.P.I.) % | # of Units | remaining in Inhaler % | remaining in Capsule % |
| D.P.I. of this invention 94.0 ± 1 | 6 | 5.7 ± 1 | 0.3 ± 1 |
| D.P.I. of Prior Art 78.1 ± 1 | 6 | 18.8 ± 1 | 3.1 ± 1 |

As appears evident from Table 1 each of the Inhaling Device of the present invention has a very excellent scattering performance with very low rate of powdered drug remaining in the Inhalers, compared with the prior art.

Thus, the present invention consists of an inhaler capable of administering powdered medicaments contained in a capsule. It is formed by a compartment housing the capsule, inside the cover or the body of the inhaler, and a cutting element, inside the same cover or the body. Said element cuts or perforates the capsule, releasing the substance it contained. The powder falls into a grid reservoir below that holds the pieces of the case end lets only the powder pass through. Once the capsule is inserted into the compartment, it will be sufficient to activate the cutting device, then place the mouthpiece into the mouth and breathe in, so that the powdered substance dispersed into the chamber can reach the lungs. Said inhaler may be equipped with disposable accessories to be placed into the mouth, otherwise may be used with specific accessories for inhaling the substances also by the nose.

While a particular form of the invention has been illustrated and described, it will be apparent that various modifications can be made without departing from the spirit and scope of the invention. Thus, although the invention has been described in detail with reference to preferred embodiments, those having ordinary skill in the art appreciate that various modification can be made without departing from the invention.

It is specified that the appearance and the basis conformation of the object described is indicative, other advantages of the device will appear to those skilled in the art from the containing of the appended drawings.

It will be readily appreciated that the forms of the invention described above are intended for purposes of illustration only, and numerous changes in the details of construction and materials employed may be made without departing from the spirit of the invention or the scope of the appended claims.

BRIEF DESCRIPTION OF DRAWINGS

FIGS. 1 and 2 show respectively the side sectional view and the frontal view of the inhaler in the first embodiment. The device is formed by a vertical chamber (1) equipped with an opening on the top, and a horizontal chamber (2) at the opposite end, which is connected and perpendicular to the vertical chamber (1) and is closed at the bottom by a chamber (3) locked to it; the vertical chamber (1) is closed on the top by a cover (5) that can move in a vertical direction, thanks to an elastic spring (6), so permitting the incision of the capsule (4) by means of a pointed element (8) fixed at the end of a rectangular support (7) connected to the cover (5). The capsule (4) is cut by means of said cover (5), which comprises a rectangular support (7), connected to the same cover (5) and having a pointed element (8) that passes through the spring (6). When the cover (5) is pressed downwards, it will perforate the capsule (4) placed into the specific compartment (13) of the horizontal chamber (2). Consequently, the pieces of the case remain in the reservoir (11), while the powdered drug is released into the chamber (12) and then inhaled by the user through the mouthpiece (16). The chamber (3) comprises, in the portion immediately before the final part of the mouthpiece (16) of the inhaler, a porous filter (17) capable of holding any possible piece of the drug not completely pulverized, so preventing their inhalation by the user. In order to ensure a greater stability of the spring (6) and to prevent the capsule (4) from moving from its compartment (13), fingers (16a) and (16b) are placed in a horizontal position above the capsule (4), consisting of a circular bend, resting on the outer edge of the hollow portion (10), and a central hole allowing the pointed element (8) to pass through the opening (9). The vertical movement of the cover (5) makes its upper part run downwards pressing the spring (6) and making the point (8) of the cutting element (7) perforate the capsule (4); by releasing the cover (5), it comes back in its initial position, by stopping upwards where its external upper protrusions (14a, 14b) meet the internal protrusions (15a, 15b) of the chamber (1).

FIGS. 3 and 4 show respectively the side sectional view and the frontal view of the inhaler in a solution that is conceptually similar to the one described in FIGS. 1 and 2, but in this embodiment, the device is formed by two chambers, exchanged each other and respectively turned of 90° compared to the previous embodiment. The horizontal chamber (1) is equipped with an opening on one end, and a vertical chamber (2) at the opposite end, which is connected and perpendicular to the horizontal chamber (1) and is closed at the bottom by a chamber (3) connected to it; the horizontal chamber (1) is closed on one of its sides by a cover (5) that can move in a horizontal direction, thanks to an elastic spring (6), so permitting the incision of the capsule (4) by means of a pointed element (8) fixed at the end of a rectangular support (7) connected to the cover (5). The capsule (4) is cut by means of said cover (5), which comprises a rectangular support (7), connected to the same cover (5) and having a pointed element (8) that passes through the spring (6). When the cover (5) is pressed by one side, it will perforate the capsule (4) placed inside the vertical chamber (2). Consequently, the pieces of the case remain inside the reservoir (11), while the powder is released into the chamber (12) and then inhaled by the user through the mouthpiece (16). The chamber (3) comprises, in the portion immediately before the final part of the mouthpiece (16) of the inhaler, a porous filter (17) capable of holding any possible piece of the drug not completely pulverized, so preventing their inhalation by the user.

FIG. 5 is an exploded view of the same device depicted in FIGS. 3 and 4, showing schematically the following elements: the cover (5) of the horizontal chamber (1) with the cutting element (7) and its pointed end (8) permitting the incision of the capsule (4); the elastic spring (6) allowing the cover (5) to move, by simply pressing on it with a finger; the vertical chamber (2), which comprises the compartment (13) housing the capsule (4), the opening (9) connecting the horizontal chamber (1) with the vertical chamber (2), inside which the cutting element (7) connected to the cover (5) runs together with its pointed end (8) that permits the incision of the capsule (4); the grid reservoir (11) holding the pieces of the case inside and letting the powder disperse in the chamber (12); the lower supporting part is additionally closed by a base (18). In order to ensure a greater stability of the spring (6) and to prevent the capsule (4) from moving from its place, a pair of fingers (16a) and (16b) are placed in a horizontal position on one side of the capsule (4), consisting of a circular bend fixed to the outer edge of the hollow portion (10) and a central hole allowing the pointed end (8) of the cutting element (7) to pass through the opening (9). The horizontal movement of the cover (5) makes its upper part run laterally towards the inside of the chamber (2), pressing the spring (6) and making the point (8) of the cutting element (7) perforate the capsule (4); by releasing the cover (5), it comes back in its initial position, by stopping where its external side protrusions (14a, 14b) meet the internal protrusions (15a, 15b) of the chamber (1)

FIG. 6 shows two top views from two different heights: the first view shows the invention composed by all its parts, particularly with the compartment (13) where the capsule (4) is located; the second view refers to a horizontal plane placed, with reference to FIG. 5, at the height relative to the view a—a, showing the grid reservoir (11) that holds the pieces of the case and lets the powder disperse in the chamber (12).

In FIG. 9, it's possible to note the vertical porous grid (17).

FIG. 14 shows a horizontal view from the height of the cutting element (7G); FIG. 15 shows a horizontal view from the height of the chamber (3).

FIG. 18 shows the side sectional view of the inhaler in a fifth embodiment. In this solution, the device is formed by a single horizontal chamber (1), equipped with an opening on the top, and closed at the bottom by a chamber (3) connected to it; the horizontal chamber (1) is closed on the top by a cover (3H) that comprises by one side, so not at the centre, a circular hole connected to the compartment (4H) where the capsule (4) is placed for its incision, in order to release the powder. The capsule (4) is split by means of a cutting element (6H) placed inside the horizontal chamber (1). The cutting element (6H) consists of a circular plate comprising a hole (7H) whose vertical axis is laterally moved from the one of the inhaler. The element (6H) can cut the lower part of the capsule (4) by means of a blade (8H) located on the lower part of the same element (6H). The rotation of the cover (3H) will cause the incision of the capsule (4) placed in the specific compartment (4H), when the blade plate (8H) under the element (6H) touches the lower part of the capsule staying inside the hole (7H) of the cutting element (6H). After the cutting element (6H) has split the capsule (4) placed in the specific compartment (4H) of the horizontal chamber (1), the pieces of the case remain inside the reservoir (11), while the powder is released into the chamber (12) and then inhaled by the user through the mouthpiece (16). The chamber (3) comprises, in the portion immediately before the final part of the mouthpiece (16) of the inhaler, a porous filter (17) capable of holding any possible piece of the drug not completely pulverized, so preventing their inhalation by the user. The system of collection of the pieces of the case inside the reservoir (11) is exactly the same as the solution described in the above figures. The rotation of the cover (3H) makes its inner part rotate inside the horizontal chamber (1), so allowing the cutting element (6H) to split the capsule (4); by releasing the cover (3H), it stops where its two outer protrusions (12a, 12b) meet the inner protrusions (13a, 13b) of the horizontal chamber (1).

FIGS. 19 and 20 show respectively the frontal and side non-sectional view of the invention where it's possible to easily identify all the elements above mentioned and described.

FIG. 21 is an exploded view of the invention that shows schematically the following elements: the cover (3H) of the horizontal chamber (1); the cutting element (6H), with the portion where the base of the capsule (4) is placed for its incision in order to disperse the powdered drug; the horizontal chamber (1), connected to the chamber (3), with the blade plate (8H) under the element (6H), the grid reservoir (11) that holds the pieces of the case of the capsule (4) and lets the powdered drug disperse into the chamber (12) in order to be inhaled by the user through the mouthpiece (16); the base (18) of the device that completely closes the chamber (3) at the bottom.

FIG. 22 shows schematically the element (6H), located inside the chamber (1), with the circular hole (7H).

FIG. 23 shows an accessory that must be placed over the mouthpiece (16) for a more hygienic use of the inhaler and can be thrown away and substituted after each use, in the case the inhaler might be used more times. It's made of rubber and comprises one portion (20) that covers the mouthpiece (16), and one portion (21) that is placed into the user's mouth in order to inhale the substance. The protrusion (22) locks the accessory to the inhaler, so preventing it from accidentally escaping. The arrow indicates the direction followed by the substance that must be inhaled.

Figure 7:
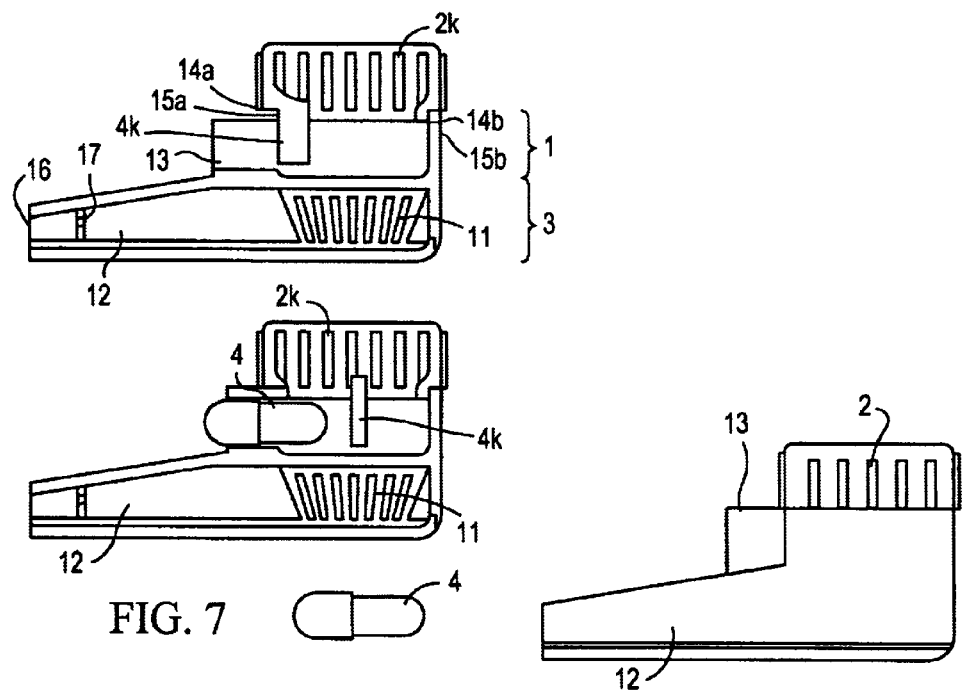
FIG. 7 shows the side sectional view of the inhaler in a third embodiment. In this solution the device is formed by a single horizontal chamber (1), equipped with an opening on the top and closed at the bottom by a chamber (3) connected to it; the horizontal chamber (1) is closed on the top by a cover (2K) that rotates, so permitting the incision of the capsule (4) by means of a thin blade element (4K) attached to the inner edge of the cover (2K). The capsule (4) is cut by means of said cover (2K), which comprises a thin blade element (4K), connected to the same cover (5). The circular rotation of the cover (2K) makes it possible to cut the capsule (4) placed into the specific compartment (13) of the horizontal chamber (1). Consequently, the pieces of the case remain inside the reservoir (11), while the powder is released into the chamber (12) and then inhaled by the user through the mouthpiece (16). The chamber (3) comprises, in the portion immediately before the final part of the mouthpiece (16) of the inhaler, a porous filter (17) capable of holding any possible piece of the drug not completely pulverized, so preventing their inhalation by the user. The system of collection of the pieces of the case inside the grid reservoir (11) is exactly the same as the solution described in Tables 1 and 2.
Figure 8:
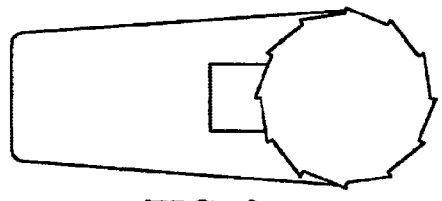
FIGS. 8, 9 and 10 show respectively the side, frontal and top view of the invention, through which it's possible to easily identify all the elements above mentioned and described. The rotation of the cover (2K) makes its inner part rotate inside the horizontal chamber (1), so that the cutting element (4K) can split the capsule (4); by releasing the cover (2K) it stops where its two outer protrusions (14a, 14b) meet the inner protrusions (15a, 15b) of the horizontal chamber (1).
Figure 9:
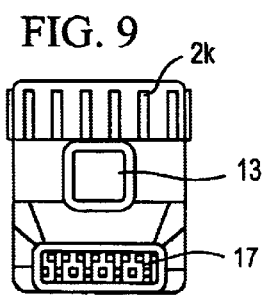
Figure 10:
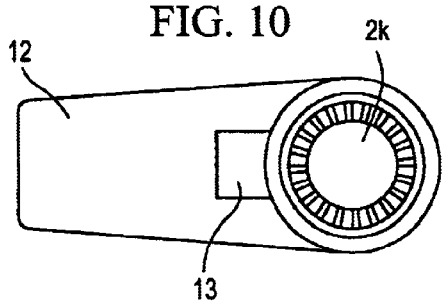
Figure 11:
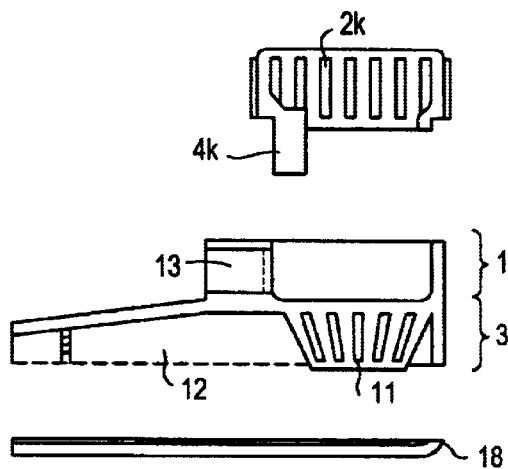
FIG. 11 is an exploded view of the invention that shows schematically the following elements: the cover (2K) of the horizontal chamber (1), with the thin blade element (4K), connected to it, which permits the incision of the capsule (4); the chamber (1), with the compartment (13) where the capsule (4) is placed; the chamber (3), with the grid reservoir (11) that holds the pieces of the case of the capsule (4) and lets the powdered drug disperse into the chamber (12); the base (18) of the device that completely closes the chamber (12) and the entire inhaler accordingly.
Figure 12:
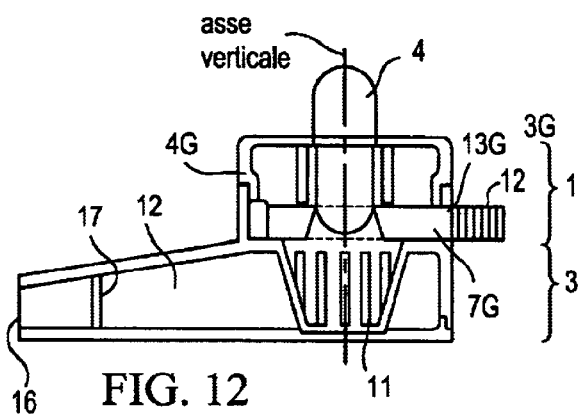
FIGS. 12 and 13 show respectively the side and frontal sectional view of the inhaler in a fourth embodiment. In this solution, the device is formed by a single horizontal chamber (1), equipped with a notch (3G) on the top, and closed at the bottom by a chamber (3) connected and locked to it. The capsule (4) is inserted into the specific compartment (13) through the notch (3G) on the top of the horizontal chamber (1) and at the centre of the element (4G). The capsule (4) is split by means of a cutting element (7G) placed inside the horizontal chamber (1) and having a central hole (8G), whose vertical axis coincides with the one of the inhaler. The element (7G) will split the capsule (4) as it rotates around a fixed point (9G) by means of a rotating hinge that locks it to the chamber (1). The rotation of the element (7G) can be easily performed by pressing with a finger on the end portion (12G) of the same element (7G), opposite to the fixed point (9G), where it is locked by a hinge to the chamber (1), from which it comes out through the hole (13G) on one side of the chamber (1). The cutting element (7G) splits the capsule (4) placed into the specific compartment (13) of the horizontal chamber (1), so that the powder and the pieces of the case fall into the reservoir (11), which lets only the powder enter the chamber (12) in order to be inhaled by the user through the mouthpiece (16). The chamber (3) comprises, in the portion immediately before the final part of the mouthpiece (16) of the inhaler, a porous filter (17) capable of holding any possible piece of the drug not completely pulverized, so preventing their inhalation by the user. The system of collection of the pieces of the case inside the grid reservoir (11) is exactly the same as the solution described in Tables 1 and 2.
Figure 13:
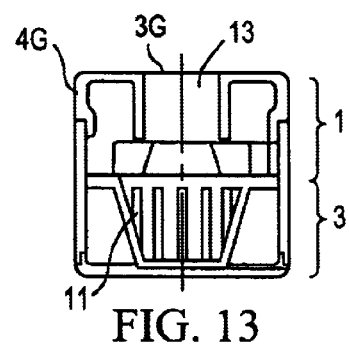
Figure 14:
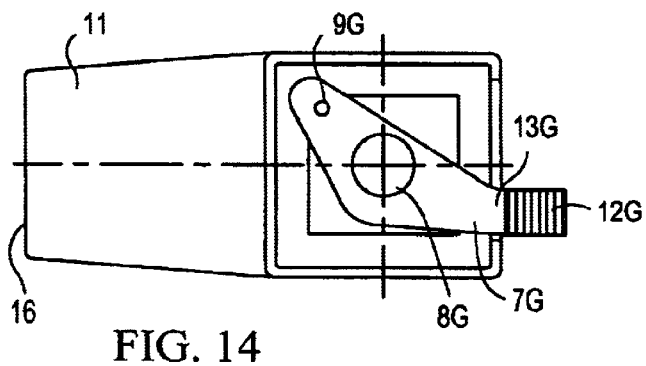
FIGS. 14 and 15 show respectively two top views from two different heights.
Figure 14B:
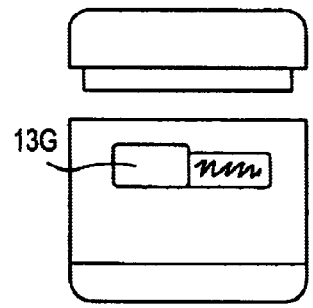
FIG. 14B shows schematically a back view of the invention, with the chambers (1) and (3). In the chamber (3) it's possible to note the hole (13G) from which the end portion (12G) of the element (7G) comes out, allowing the user to press on it, laterally, with a finger, in order to split the capsule (4).
Figures 15, 16:
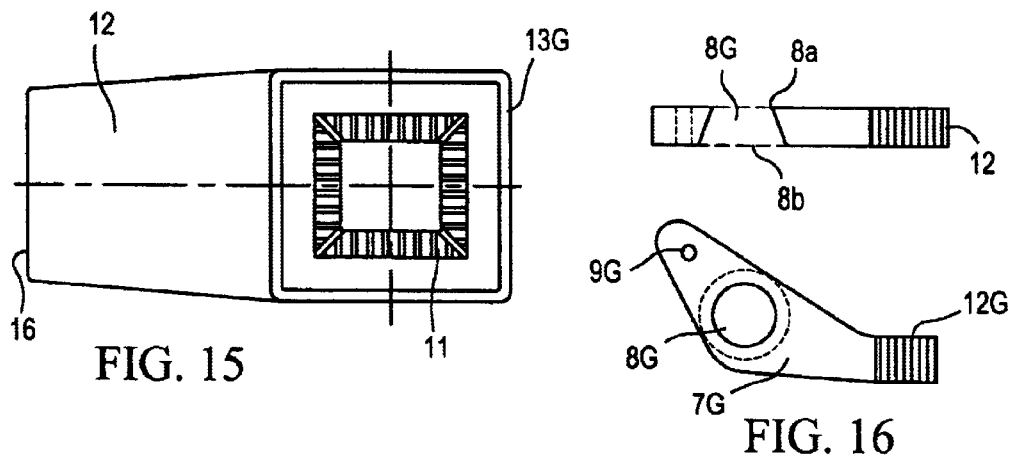
FIG. 16 shows schematically the element (7G) from the side and top view.
Figure 17:
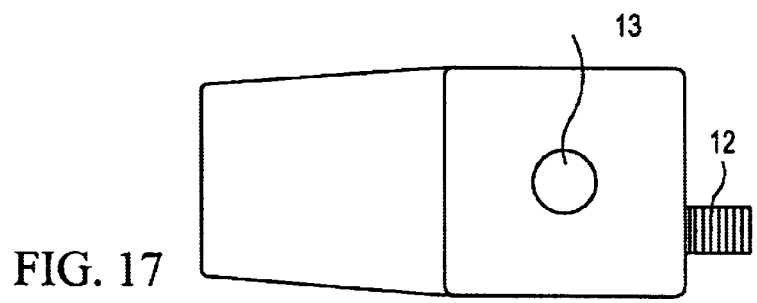
FIG. 17 is a top non-sectional view of the inhaler, in the embodiment depicted in FIGS. 12, 13, 14, 14B and 15. Also in this drawing, it's possible to easily identify all the elements above mentioned and described.
Figures 18, 19:
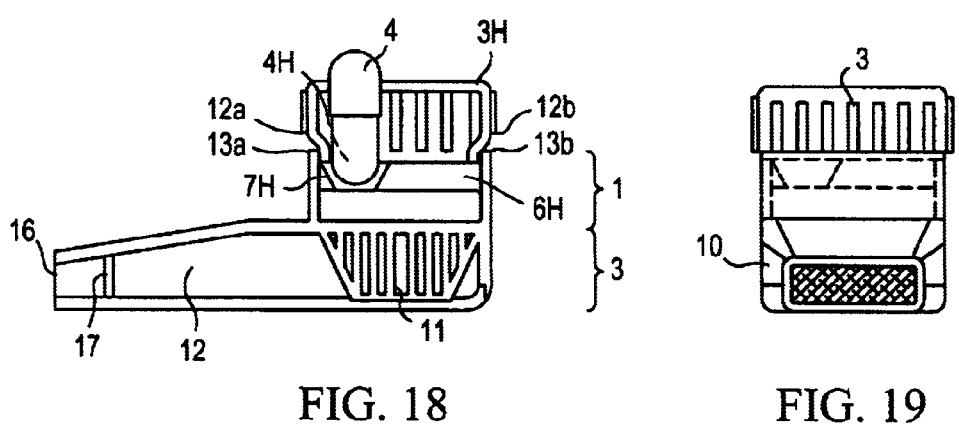

The present invention provides the following advantages: An Inhaling device for dispersing through the respiratory tract only one dose of powdered medicaments contained in a capsule at a time, characterized in that it comprises:
  means to hold the capsule (4) with a compartment (13), located inside the cover or inside the chamber close to it, into which the capsule is inserted for about half its length and is held still during the operation of incision so as to guarantee the dispersion of the powder it contains;
  means to split the capsule, with a cutting element equipped, on one end, with a blade and/or point;
  means to release the powder contained in the capsule, with a body formed by one or more chambers (1) (2) that contain the capsule and the cutting device, connected to a chamber (3) set to hold the powder produced after the breakage of the capsule;
  means to hold the pieces of the case of the capsule, after it has been split, and to prevent the powder from aggregating, with a reservoir (11) having a series of slots on its walls that hold the bigger pieces inside, while letting the powder enter the chamber (12);
  means to deliver the powder of the capsule released into the lower chamber of the inhaler, with a mouthpiece (16) from which the user can inhale the powder;

optional means to filter the powdered drug, in the portion immediately before the final part of the opening of the inhaler, with a porous filter (17) capable of holding any possible piece of the drug not completely pulverized.

An additional advantage dependent upon the first advantage is an Inhaling device, characterized in that the capsule is cut by the point connected to the cover, which moves up and down by means of a spring. This system comprises:

means to hold and split a capsule (4) and then release the powder it contained, with a body consisting of a chamber (1), equipped with a cover (5) at one end, and a chamber (2) at the opposite end, which is connected to said chamber (1) and is closed at the bottom by a chamber (3) connected to said chamber (2);

means to hold the capsule inside said chamber (2), with an open compartment (13) into which the capsule (4) is placed, resting on the circular groove of said compartment (13), and filling the hollow portion (10) of the chamber (2);

means to hold the pieces of the case of the capsule (4), after it has been split, and to prevent the powder from aggregating, with a grid reservoir (11) having a series of slots on its walls that hold the bigger pieces inside, while letting the powder pass through;

means to close the container comprising the capsule, with a cover (5) which enters the chamber (1) and has two outer protrusions (14a, 14b) on its walls that stop under the inner protrusions (15a, 15b) of the chamber (1), preventing the cover from accidentally escaping from its place;

means to allow the cover (5) to move perpendicularly to the capsule (4) till the stop of said protrusions, with a spring (6) inside the chamber (1), which touches the outer edge of the hollow portion (10) on its lower side and the inner surface of the cover on its upper side;

means to split the capsule (4), with said cover (5) having inside a pointed element (7) that passes through the elastic spring (6); when the cover (5) is pressed, it will perforate the capsule (4) placed into the hollow portion (10), releasing its powder into the chamber (12) and holding the pieces of the case in the reservoir (11);

means to deliver the powder of the capsule (4) released into the chamber (12), with a mouthpiece (16) from which the user can inhale the powder.

An additional advantage dependent upon the second advantage is an Inhaling device characterized in that the capsule (4) is located inside the compartment (13) in the hollow portion (10) in a horizontal position, when the cover (5) is vertical, or in a vertical position, when the cover (5) is horizontal; in this way, the element (7) will perforate the capsule (4) with its point (8), when the cover (5) is pressed respectively down, in a vertical and perpendicular direction towards the capsule, or laterally, in a horizontal and perpendicular direction towards the same capsule.

An additional advantage dependent upon the second advantage is an Inhaling device characterized in that the operation of incision of the capsule and the consequent inhalation of the powdered drug by the user, can be easily performed using just one hand: in particular, it's sufficient to keep the inhaler with your right hand, place your thumb under the base of the inhaler supporting it, and press the cover with your forefinger, so as to perforate the capsule and let the powder disperse into the chamber (12) below, after it has been filtered by the reservoir (11); then you place the device into your mouth and inhale the powdered drug.

A further advantage dependent upon the second advantage is an Inhaling device characterized in that the body of the inhaler is formed by three parts that can be assembled each other: the chambers (1) and (2), and the chamber (3), besides a cover (5) that enters the chamber (1). Such a conformation facilitates the manufacturing and assembling of this device, considerably reducing the costs of the mass production.

An additional advantage dependent upon the first advantage above, is an Inhaling device characterized in that the capsule is cut by means of the rotation of the cover of the inhaler. This system comprises:

means to hold and split a capsule (4) and then release the powdered drug it contained, with a body consisting of a single chamber (1) in a horizontal position, equipped with an opening on the top, and closed at the bottom by a chamber (3) connected to it, so forming a single element;

means to hold the capsule inside the chamber (1), with an open compartment (13) into which the capsule (4) is placed in a horizontal position, resting on the circular groove of said compartment (13);

means to hold the pieces of the case of the capsule (4), after it has been split, and to prevent the powder from aggregating, with a reservoir (11), under the division point of the capsule, having a series of slots on its walls that hold the bigger pieces inside, while letting the powder pass through;

means to close the container (1) comprising the capsule, with a cover (2K) that closes the upper end of the chamber (1) and has two outer protrusions (14a, 14b) on its walls that stop under the inner protrusions (15a, 15b) of the horizontal chamber (1), preventing the cover (2K) from accidentally escaping from its place;

means to split the capsule (4), with a thin blade element (4K), connected to the cover (2K) and attached to its inner edge;

means to allow the cover (2K) to rotate, thanks to the circular shape of the same cover (2k) and the chamber (1), so as to split the capsule (4) with a simple rotation of the cover, in any direction, till the element (4K) reaches and cuts the capsule (4);

means to deliver the powder of the capsule (4) released into the chamber (3), with a mouthpiece (16) from which the user can inhale the powdered drug.

An additional advantage dependent upon the sixth advantage above, is an Inhaling device characterized in that the blade element (4k) is connected and perpendicular to the cover (2K) and to the capsule (4), so that, as it rotates following the rotation of the cover, it will cut part of the case of the capsule, removing it and letting the powder and the pieces of the same case fall into the reservoir (11) below, which lets only the powder enter the chamber (12) in order to be inhaled. In this solution, the body of the inhaler is formed by two parts that can be assembled each other: the chambers (1) and (3), connected each other, besides the cover (2K) that enters the horizontal chamber (1).

A further advantage dependent upon the sixth advantage above, is Inhaling device characterized in that the operation of incision of the capsule and the consequent inhalation of the powdered drug by the user, can be easily performed by keeping the inhaler with one of your hands, and rotating the cover (2K) with the other one, until the blade element (4K) connected to the cover (2K) touches the lower part of the capsule (4); then you place the device into your mouth and inhale the powdered drug.

An additional advantage dependent upon the sixth advantage above, is an Inhaling device characterized in that the capsule (4) is inserted by the side wall of the chamber (1) into the suitable compartment (13), in a horizontal position. In order to prevent the capsule (4) from moving from its place, the lower edge of the cover (2K) has two outer protrusions (14a, 14b) on its walls that stop under the inner protrusions (15a, 15b) of the horizontal chamber (1), preventing the cover (2K) from accidentally escaping from its place and, at the same time, ensuring a greater stability of the capsule (4) during the operation of its incision.

A further advantage dependent upon the first advantage above, is an Inhaling device characterized in that the capsule is split by means of a cutting element that moves inside the unique horizontal chamber. This system comprises:

means to hold a capsule and then release the powder it contained, with a body consisting of a single chamber (1) in a horizontal position, equipped with an opening on the top, and connected at the bottom to a chamber (3) locked to it;

means to hold the capsule inside the only horizontal chamber (1), with an upper open compartment (13) into which the capsule (4) is placed in a vertical position, resting on the circular groove of said compartment (13);

means to hold the pieces of the case of the capsule (4), after it has been split, and to prevent the powder from aggregating, with a grid reservoir (11) below;

means to split the capsule (4), with a cutting element (7G), located inside the horizontal chamber (1), which comprises a system of two circular holes (8G) holding the lower part of the capsule (4) and having a vertical axis that coincides with the one of the inhaler;

means to allow the cutting element (7G) to move, with a rotating hinge at the end of the same element (7G) connected to an inner corner of the chamber (1), so that by pressing with a finger on the end portion (12G) of the cutting element (7G), it splits the capsule (4) in a horizontal direction, causing the dispersion of the powdered drug that will be later inhaled by the user;

means to deliver the powder of the capsule (4) released into the chamber (12), with a mouthpiece (16) from which the user can inhale the powder.

An additional advantage dependent upon the tenth advantage above, is an Inhaling device characterized in that, by pressing the end portion (12G) of the cutting element (7G), the hole (8G), which has a cutting inner perimeter and comprises a part of the capsule (4), moves in a horizontal direction, so that it removes the lower part of the case, letting the powder fall into the reservoir (11) below, together with the pieces of the case. 12) Inhaling device according to claim 10, characterized in that the cover is fixed and the capsule is inserted in a vertical position into the compartment (13) inside the cover, through a notch (3G) on the upper part of the cover.

An additional advantage dependent upon the tenth advantage above is an Inhaling device characterized in that the hole (8G) of the cutting element (7G) that must split the capsule (4) located into the specific compartment (13), is formed by two circular holes of different diameter, having corresponding vertical axis with each other and with the vertical axis of the inhaler. The diameter of the hole (8a) on the upper part of the element (7G) is suitably smaller than the diameter of the hole (8b) on the lower part of the element (7G). This ensure a greater stability of the capsule (4) during the operation of its incision by means of the rotation of the element (7G); all that involves a complete dispersion of the powdered drug, preventing the capsule from moving upwards and consequently losing powder from the upper notch (3G) of the chamber (1).

A further advantage dependent upon the tenth advantage above is an Inhaling device characterized in that the body of the inhaler is formed by two parts that can be assembled each other: the chambers (1) and (3), connected each other, besides a cover (4G) that perfectly enters, by its lower edge, the horizontal chamber (1). In this solution, the operation of incision of the capsule (4) and the consequent inhalation of the powdered drug by the user, can be easily performed by keeping the inhaler with one of your hands, and making the cutting element (7G) move with the other one, so that you press with your thumb on the end portion (12G) causing the element (7G) rotate around the fixed point (9G) where a rotating hinge is located.

An additional advantage dependent upon the tenth advantage above, is an Inhaling device characterized in that the cutting element (7G) is made of plastic or other suitable material ensuring the necessary stiffness, so that it's sufficient a moderate force to split the capsule by means of the rotation of the cutting element.

An additional advantage dependent upon the first advantage above, is an Inhaling device characterized in that the capsule is cut by means of the rotation of the cover of the inhaler. This system comprises:

means to hold a capsule (4) and then release the powder it contained, with a body consisting of a chamber (1) in a horizontal position, equipped with an opening on the top and closed at the bottom by a chamber (3) connected to it. The horizontal chamber is closed on the top by a cover (3H) that comprises a compartment (13) of circular shape, inside which the capsule (4) is directly placed in a vertical position,;

means to hold the capsule inside said cover (3H), with an open compartment (13), of circular shape, placed directly inside the cover (3H), into which the capsule (4) is placed, resting on the circular groove of said compartment (13);

means to hold the pieces of the case of the capsule (4), after it has been split, and to prevent the powder from aggregating, with a reservoir (11) having a series of slots on its walls that hold the bigger pieces inside, while letting the powder pass through;

means to close the container (1), with a cover (3H), which holds the capsule (4) and closes the horizontal chamber (1), having two outer protrusions (12a, 12b) on its walls that stop under the inner protrusions (13a, 13b) of the chamber (1), preventing the cover (3H) from accidentally escaping from its place;

means to allow the cover (3H) to rotate, thanks to the circular shape of the same cover (3H) and the chamber (1), so as to split the capsule (4) with a simple rotation of the cover, in any direction, till a blade element (8H) reaches and cuts the capsule (4);

means to split the capsule (4), with an element (6H), consisting of a circular plate comprising a hole (7H), whose vertical axis is laterally moved from the one of the inhaler, which holds the lower part of the capsule (4), so that, by rotating said element (6H), the blade (8H) below cuts the lower part of the capsule (4);

means to filter the powder and the pieces of the case, with a reservoir (11) under the division point;

means to deliver the powder of the capsule released into the chamber (12), with a mouthpiece (16) from which the user can inhale the powder.

An additional advantage dependent upon the sixteenth advantage described above, is an Inhaling device characterized in that the lower part of the capsule (4) is inserted both into the hole of the element (6H) and into the corresponding hole below (7H) of the blade element (8H), which has a cutting inner circumference, so that, as the element (6H) rotates, while the blade element (8H) below is fixed, it will remove the lower part of the capsule (4), letting the powder fall into the reservoir.

An additional advantage dependent upon the sixteenth advantage described above is an Inhaling device characterized in that the rotation of the cover (3H) permits the incision of the capsule (4); in this case, the capsule (4) remains in the specific compartment (13) that holds its upper part still, while its lower part is cut by the hole (7H) where it is inserted, following the rotation of the same cover.

A further advantage dependent upon the sixteenth advantage described above is an Inhaling device characterized in that the capsule is directly inserted by the upper edge of the cover (3H), in a vertical position, corresponding to the external edge of the same cover (3H). In order to prevent the capsule (4) from moving from its place, the lower edge of the cover (3H) has two outer protrusions (12a, 12b) on its walls that stop under the inner protrusions (13a, 13b) of the horizontal chamber (1), preventing the cover (3H) from accidentally escaping from its place and, at the same time, ensuring a greater stability of the capsule (4) during the operation of its incision.

An additional advantage dependent upon the sixteenth advantage described above is an Inhaling device characterized in that the body of the inhaler is formed by two parts that can be assembled each other: the chambers (1) and (2), connected each other, besides a cover (3H) that enters the horizontal chamber (1). In this solution, the operation of incision of the capsule and the consequent inhalation of the powdered drug by the user, can be easily performed by keeping the inhaler with one of your hands, and rotating the cover (3H) with the other one, until the element (6H) connected to the cover (3H) touches the lower part of the capsule (4); then you place the device into your mouth and inhale the powdered drug.

An additional advantage dependent upon the previous advantages is an Inhaling device characterized in that an accessory can be additionally provided (FIG. 23): it's made of rubber or other suitable material and must be placed over the mouthpiece (16) of the inhaler, where it is locked thanks to its protrusion (22). In this way, the user inhales the powder from its opening (21) and substitutes the covering after each use.

An additional advantage dependent upon the previous advantages is an Inhaling device characterized in that it can be conveniently and easily carried, thanks to its small size, and can simplify and reduce the operations that must be performed for the inhalation of the powdered drug by the user. In particular, the shape and the position of the various chambers of the invention allow the user to perform the operation of incision of the capsule and the consequent inhalation of the powdered drug with a single hand, using a single finger to cause the incision of the capsule, a different finger according to each different solution. With the rest of the hand, he/she places the device into his/her mouth and inhales the powdered drug.

An additional advantage dependent upon the previous advantages is an Inhaling device characterized in that the powder released into the device is inhaled by the user by placing the outer end of the chamber, opposite to the grid reservoir, into his/her mouth or nose and breathing in, so that the powder coming out from the opening enters the mouth or nose and reaches the lungs.

An additional advantage dependent upon the previous advantages is an Inhaling device characterized in that it is made of plastic material and should be thrown away after each use, so as to guarantee the greatest comfort.

An additional advantage dependent upon the previous advantages is an Inhaling device characterized in that, under the housing portion of the capsule, a reservoir is provided, with a series of slots on its walls and a grid shape, which allows the pieces of the case of the capsule to remain inside the reservoir. Said reservoir has the important function to prevent the powder from aggregating in a humid atmosphere, obstructing in this way its dispersion into the chamber and the consequent inhalation by the user.

An additional advantage dependent upon the previous advantages is an Inhaling device characterized in that the spring (6) is made of metal, plastic or other suitable material ensuring the right flexibility, so that it's sufficient a moderate pressure to make it move.

An additional advantage dependent upon the previous advantages is an Inhaling device characterized in that, in order to prevent the capsule (4) from moving from its place, and ensure a greater stability of the spring (6), fingers (16a) and (16b) are placed above or on one side of the capsule, accordingly to its horizontal or vertical position, consisting of a circular bend resting on the outer edge of the hollow portion (10) and a central hole allowing the point (8) of the cutting element (7) to pass through.

An additional advantage dependent upon the previous advantages is an Inhaling device characterized in that, with reference to the figures of Tables 3/7 and 5/7, the cutting element is made of plastic or other suitable material ensuring the necessary stiffness, so that it's sufficient a moderate force to split the capsule by means of the rotation of the cover. Additionally, the cover can be totally pulled out from the horizontal chamber (1), so permitting to substitute the old capsule with a new one, in the case this device might be used more times.

We claim:

1. An inhaling device for dispersing through the respiratory tract only one dose of powdered medicaments contained in a capsule at a time, said device comprising:
    externally accessible means for holding the capsule within a compartment inside said inhaling device;
    means for splitting the capsule without any significant movement of the capsule
    means for releasing the powdered medicaments contained in the capsule, said capsule enclosed in an outer case;
    means for holding pieces of the case of the capsule after said case has been split and to prevent the powdered medicaments from aggregating; and
    means for delivering to a user the powdered medicaments of the capsule released into the inhaling device.

2. The inhaling device according to claim 1 wherein said compartment is located inside a cover or inside one or more chambers within said device, said compartment proximate said means for holding said capsule, into which the capsule is inserted and held therein during operation of incision of said capsule so as to guarantee proper dispersion of the powdered medicaments contained in the capsule.

3. The inhaling device according to claim 2 wherein said means for splitting said capsule is comprised of a cutting element, said cutting element comprised of a blade or pointed element.

4. The inhaling device according to claim 1 wherein said means for delivering the powdered medicaments includes a mouthpiece from which the user can inhale the powdered medicaments.

5. The inhaling device according to claim 3, wherein the cutting element that cuts the capsule moves up and down by means of a spring.

6. The inhaling device of claim 5 wherein said means for holding the capsule comprises a body, said body comprising a first chamber with said cover at one end, a second chamber cooperatively connected to said first chamber at said first chamber's opposite end, and a lower chamber cooperatively connected to a bottom end of said second chamber, said lower chamber including an aperture therein, said aperture adapted to house the powdered medicaments produced after breakage of the capsule thereby facilitating manufacturing and assembling and considerably reducing costs of the mass production of the device.

7. The inhaling device of claim 6 wherein said compartment into which the capsule is placed further comprises a circular groove, and said second chamber further comprises a hollow portion wherein said capsule rests upon said circular groove and fills the hollow portion.

8. The inhaling device of claim 7 wherein said means to hold the pieces of the case of the capsule after said capsule has been split and to prevent the powdered medicament from aggregating comprises a reservoir having a series of slots on its walls to hold larger, aggregated pieces of the powdered medicament inside while letting non-aggregated powdered medicament pass through thereby allowing the pieces of the case of the capsule to remain inside the reservoir, said reservoir having the function of preventing the powdered medicament from aggregating in a humid atmosphere, which may obstruct its dispersion into the lower chamber and the consequent inhalation by the user.

9. The inhaling device of claim 7 further comprising means for securing the capsule within the device, said means for securing the capsule comprising said cover having walls, which covers the first chamber, and two outer protrusions on the walls of the cover that stop under a pair of inner protrusions of the first chamber, thereby preventing the cover from accidentally escaping from its place.

10. The inhaling device of claim 9 further comprising means to allow the cover to move perpendicularly with respect to the capsule until the cover abuts the inner protrusions, wherein said spring, inside the first chamber, touches an outer edge of the hollow portion of said second chamber on its lower side and an inner surface of the cover on its upper side.

11. The inhaling device of claim 8 wherein said pointed element within said cover passes through said spring whereby when pressure is applied to the cover, the pointed element will perforate the capsule placed into the hollow portion, thereby releasing the powder medicament into the aperture of said lower chamber and holding pieces of the case in the reservoir.

12. The inhaling device according to claim 7, wherein the capsule is located in the hollow portion of said compartment in a substantially horizontal position when the cover is vertical, or in a substantially vertical position when the cover is horizontal thereby allowing the cutting element to perforate the capsule when the cover is pressed respectively down in a vertical and perpendicular direction towards the capsule, or laterally, in a horizontal and perpendicular direction towards the capsule.

13. The inhaling device according to claim 3, wherein the operation of incision of the capsule and consequent inhalation of the powdered medicament by the user can be performed by holding the inhaling device with one hand, and rotating the cover with the other hand until the cutting element connected to the cover touches a lower part of the capsule and the device is placed in the user's mouth and the powdered drug inhaled.

14. The inhaling device according to claim 4, further comprising an accessory made of rubber or other suitable material that is placed over the mouthpiece of the inhaling device, where it is locked thereto due to a flange thereby allowing the user to inhale the powdered medicament from an opening in the mouthpiece.

15. The inhaling device according to claim 1, wherein said device can be conveniently and easily carried, due to its small size, and can simplify and reduce operations that must be performed for the inhalation of the powdered medicament by the user, the shape and position of the chambers of the device allowing the user to perform the operation of the incision of the capsule and consequent inhalation of the powdered medicament with a single hand, using a single finger to cause the incision of the capsule, while with the rest of the hand of the user can place the device into his or her mouth and the powdered medicament inhaled.

16. The inhaling device according to claim 8, wherein the powdered medicament is released into the device is inhaled by the user by placing the outer end of said lower chamber opposite said reservoir into his or her mouth or nose and breathing in so that the powdered medicament coming out from the mouthpiece enters the mouth or nose and reaches the lungs.

17. The inhaling device according to claim 1, wherein the device is made of plastic material and may be disposed of after each use, so as to guarantee the greatest comfort.

18. The inhaling device according to claim 5, wherein the spring is made of metal, plastic or other suitable material ensuring proper flexibility, such that sufficiently moderate pressure will make the spring move.

19. The inhaling device according to claim 7, wherein in order to prevent the capsule from moving from its place, and to ensure greater stability of the spring, a pair of projections are placed above or on one side of the capsule, depending upon its horizontal or vertical position, said projections consisting of a circular bend resting on an outer edge of said hollow portion of said second chamber and a central orifice allowing the pointed element of the cutting element to pass through.

20. The inhaling device according to claim 6, wherein the cutting element is made of plastic or other suitable material ensuring the necessary stiffness, such that a moderate force is sufficient to split the capsule by means of the rotation of the cover, the cover adapted to be totally pulled out from the first chamber, thereby allowing substitution of an old capsule with a new capsule, when it is desired to use the device multiple times.

21. The inhaling device of claim 1 further comprising means for filtering the powdered medicaments, said means for filtering comprising a porous filter capable of holding any possible piece of the powdered medicament not completely pulverized.

22. An inhaling device for dispersing through the respiratory tract only one dose of powdered medicaments contained in a capsule at a time, said capsule enclosed within a case, wherein said capsule is split by means of rotating a cover of the inhaling device, said device comprising:

means to hold and split the capsule and then release the powdered medicaments contained therein, comprising a body having a substantially horizontal chamber, said horizontal chamber in a substantially horizontal position and equipped with an opening at its top, said horizontal chamber cooperatively communicating with a lower chamber at its bottom, said lower chamber comprising an aperture, thereby forming a single element;

means to hold the capsule inside the horizontal chamber, having an open compartment into which the capsule is placed in a substantially horizontal position, said capsule resting on a circular groove of said compartment;

means to hold pieces of the case of the capsule after said case has been split and to prevent the powdered medicaments from aggregating, comprising a reservoir situated under a division point of the capsule, said reservoir having a series of slots on its walls adapted to hold larger, aggregated pieces of said capsule therein, while letting the powdered medicaments pass through;

means for closing said horizontal chamber containing the capsule, said closing means comprising a cover having walls, said cover closes an upper end of the horizontal chamber, and two outer protrusions projecting from the walls of said cover that stop under two inner protrusions projecting from the horizontal chamber, thereby preventing the cover from accidentally escaping from its place and, at the same time, ensuring a greater stability of the capsule during the operation of incision;

means for splitting the capsule comprising a cutting element connected to the cover and attached to its inner edge;

means to allow the cover to rotate, said cover and said horizontal chamber each having a substantially circular shape so as to split the capsule with a simple rotation of the cover in any direction until the cutting element reaches and cuts the capsule; and means to deliver the powdered medicament of the capsule released into the chamber to a user, comprising a mouthpiece from which the user can inhale the powdered medicament.

23. The inhaling device according to claim 22 wherein said cutting element comprises a blade or pointed element.

24. The inhaling device according to claim 22, wherein the cutting element is connected and perpendicular to the cover and to the capsule, so that as said cutting element rotates and follows the rotation of the cover, the cutting element will cut part of the case of the capsule, removing it and letting the powdered medicament and pieces of the case fall into the reservoir below, said reservoir letting only the powdered medicament enter the aperture in order to be inhaled.

25. The inhaling device according to claim 22, wherein operation of incision of the capsule and consequent inhalation of the powdered drug by the user can be easily performed by the user holding the inhaling device with one hand and rotating the cover with the other hand until the cutting element connected to the cover touches a lower part of the capsule and the device is placed in the user's mouth and the powdered medicament inhaled.

26. An inhaling device for dispersing through the respiratory tract only one dose of powdered medicaments contained in a capsule at a time, said capsule enclosed within an outer case, wherein said capsule is split by means of a cutting element that moves inside a unique horizontal chamber, said inhaling device comprises:

means to hold the capsule and then release the powdered medicaments contained therein, having a body comprising a first chamber in a substantially horizontal position, said body equipped with an opening on top and connected at its bottom to a lower chamber;

means to hold the capsule inside the substantially horizontal first chamber comprising an upper open compartment into which the capsule is placed in a substantially vertical position, said capsule resting on a circular groove within said compartment;

means to hold pieces of the case of the capsule after it has been split and to prevent the powdered medicament from aggregating, said means to hold pieces of the case of the capsule comprising a grid reservoir;

means to split the capsule comprising a cutting element located inside the first chamber, said splitting means further comprising a system of one or more holes into which the capsule or a portion thereof is placed, said one or more holes having a vertical axis that coincides with a vertical axis of the inhaling device;

means to allow the cutting element to move comprising a rotating hinge at an end portion of the cutting element, said hinge connected to an inner corner of the first chamber, so that by pressing with a finger on an end portion of the cutting element, the cutting element splits the capsule in a substantially horizontal direction causing dispersion of the powdered medicament that will be later inhaled by a user; and means to deliver the powdered medicament of the capsule released into the aperture, said delivery means comprising a mouthpiece from which the user can inhale the powdered medicament.

27. The inhaling device according to claim 26, wherein, by pressing the end portion of the cutting element, said one or more holes, which have a cutting inner perimeter and comprise a part of the capsule, move in a substantially horizontal direction so that the cutting element removes the lower part of the capsule, letting the powdered medicament fall into the reservoir below, together with pieces of the case.

28. The inhaling device according to claim 26, further comprising a cover, said capsule is inserted in a substantially vertical position into the compartment inside the cover, through a notch within the upper part of the cover.

29. The inhaling device according to claim 26, wherein said one or more holes of the cutting element comprises a first hole on the upper part of the cutting element and a second hole on a lower part of the cutting element, said holes having corresponding vertical axes with each other and with the vertical axis of the inhaling device.

30. The inhaling device according to claim 29 wherein the diameter of the first hole on the upper part of the cutting element is suitably smaller than the diameter of the second hole on the lower part of the cutting element thereby ensuring greater stability of the capsule during the operation of its incision by means of rotation of the cutting element, resulting in a complete dispersion of the powdered medicament thereby preventing the capsule from moving upwards and consequently losing powdered medicament from an upper opening of the first chamber.

31. The inhaling device according to claim 26 wherein the body of the inhaling device is formed by two parts that can be assembled to each other, said first chamber and said lower chamber connected to the first chamber, said first chamber adjacent to the cover that enters, by its lower edge, the horizontal first chamber thereby allowing the operation of incision of the capsule and the consequent inhalation of the powdered medicament by the user to be easily performed by the user holding the inhaling device with one hand, and making the cutting element move with another hand by pressing with a finger on the end portion causing the cutting element to rotate around a fixed point where a rotating hinge is located.

32. The inhaling device according to claim 26 wherein the cutting element is made of plastic or other suitable material ensuring necessary stififiess, such that a sufficiently moderate force may split the capsule by means of the rotation of the cutting element.

33. An inhaling device for dispersing through the respiratory tract only one dose of powdered medicaments contained in a capsule at a time, wherein said capsule, encased within an outer case, is cut by means of the rotation of the cover of the inhaling device, said inhaling device comprising:

means to hold the capsule and then release the powdered medicaments contained therein, having a body consisting of a first chamber in a substantially horizontal position, equipped with an opening on the top and closed at the bottom by a lower chamber connected to it, said lower chamber comprising an aperture, wherein the substantially horizontal first chamber is closed on the top by a cover, said cover having walls, said first chamber comprising a compartment of substantially circular shape, inside of which the capsule is directly placed in a substantially vertical position;

means to hold the capsule inside said cover, with the open compartment placed directly inside the cover, into which the capsule is placed, said capsule resting on a circular groove of said compartment;

means to hold pieces of the case of the capsule after it has been split and to prevent the powder from aggregating, said means having a reservoir with a series of slots on its walls that holds larger, aggregated pieces inside, while letting non-aggregated powdered medicament pass through;

means to seal the cover upon the first chamber comprising two outer protrusions on the walls of said cover that stop under inner protrusions of the first chamber thereby preventing the cover from accidentally escaping from its place;

means to allow the cover to rotate due to the substantially circular shape of the cover and the first chamber, so as to split the capsule with a simple rotation of the cover in any direction, until the cutting element reaches and cuts the capsule;

means to split the capsule comprising an element, said element having a substantially circular plate with a substantially circular aperture therein, said circular aperture having a vertical axis laterally displaced from the axis of the inhaling device, and which holds a lower part of the capsule such that, by rotating said element, the cutting element cuts the lower part of the capsule;

means to filter the powdered medicament and pieces of the case, said filtering means comprising said reservoir situated under a division point of said capsule; and means to deliver the powdered medicament of the capsule released into the aperture, said means to deliver having a mouthpiece from which the user can inhale the powder.

34. The inhaling device according to claim 33, wherein the lower part of the capsule is inserted into the circular aperture of the element below the cutting element, said circular aperture having a cutting inner circumference, such that as the element rotates, while the cutting element situated below is fixed, the element will remove the lower part of the capsule thereby letting the powdered medicament fall into the reservoir.

35. The inhaling device according to claim 34, wherein the rotation of the cover permits incision of the capsule, the capsule remaining in the compartment that holds the upper part of said capsule, while the lower part of the capsule is cut by the cutting inner circumference of said circular aperture where it is inserted following the rotation of the cover.

36. The inhaling device according to claim 35, wherein the capsule is directly inserted proximate the upper edge of the cover in a substantially vertical position corresponding to an external edge of the cover in order to prevent the capsule from moving from its place, the lower edge of the cover having said two outer protrusions on its walls that stop under said inner protrusions of the horizontal first chamber, preventing the cover from accidentally escaping from its place and, at the same time, ensuring greater stability of the capsule during the operation of its incision.

37. The inhaling device according to claim 33, wherein the body of the inhaler is formed by two parts that can be assembled to each other, wherein the first chamber and a second chamber are connected to each other adjacent a cover that enters the first chamber thereby facilitating the operation of incision of the capsule and consequent inhalation of the powdered medicament, wherein the user can keep the inhaling device in one hand and rotate the cover with the other hand until the element connected to the cover touches the lower part of the capsule whereby the device is placed in the user's mouth and the powdered medicament inhaled.

* * * * *